(12) United States Patent
Furner et al.

(10) Patent No.: US 10,377,556 B2
(45) Date of Patent: Aug. 13, 2019

(54) RETAINING APPARATUS

(71) Applicant: S.C. Johnson & Son, Inc., Racine, WI (US)

(72) Inventors: Paul E. Furner, Racine, WI (US); Dirk K. Nickel, Mukwonago, WI (US)

(73) Assignee: S.C. JOHNSON & SON, INC., Racine, WI (US)

( * ) Notice: Subject to any disclaimer, the term of this patent is extended or adjusted under 35 U.S.C. 154(b) by 152 days.

(21) Appl. No.: 14/614,208

(22) Filed: Feb. 4, 2015

(65) Prior Publication Data

US 2016/0221746 A1 Aug. 4, 2016

(51) Int. Cl.
*A61L 9/14* (2006.01)
*B65D 83/20* (2006.01)
*B65D 83/38* (2006.01)

(52) U.S. Cl.
CPC ......... *B65D 83/206* (2013.01); *B65D 83/384* (2013.01); *B65D 83/388* (2013.01); *A61L 9/14* (2013.01); *A61L 2209/133* (2013.01); *A61L 2209/134* (2013.01)

(58) Field of Classification Search
CPC .. B65D 83/205; B65D 83/206; B65D 83/384; B65D 83/753; A45D 34/02
See application file for complete search history.

(56) References Cited

U.S. PATENT DOCUMENTS

| | | |
|---|---|---|
| 3,236,458 A | 2/1966 | Ramis |
| 3,304,797 A | 2/1967 | Graveley |
| 3,369,756 A | 2/1968 | Ramis |
| 3,550,857 A | 12/1970 | Ahlberg |
| 3,972,473 A | 8/1976 | Harrison |
| 4,165,835 A | 8/1979 | Dearling |
| 4,200,229 A | 4/1980 | Spector |
| 4,235,373 A | 11/1980 | Clark |
| 4,341,348 A | 7/1982 | Dearling |
| 4,346,059 A | 8/1982 | Spector |
| 4,356,969 A | 11/1982 | Obermayer et al. |
| D274,040 S | 5/1984 | Ridgley |

(Continued)

FOREIGN PATENT DOCUMENTS

| | | |
|---|---|---|
| CN | 201551616 U | 8/2010 |
| DE | 2235541 A1 | 1/1974 |

(Continued)

OTHER PUBLICATIONS

PCT/US2016/014278 International Search Report and Written Opinion dated May 3, 2016.

(Continued)

*Primary Examiner* — Nicholas J. Weiss
(74) *Attorney, Agent, or Firm* — Quarles & Brady LLP

(57) ABSTRACT

A retaining apparatus configured to couple to a valve stem of an aerosol container and to interface with a dispenser to actuate the valve stem. The apparatus includes a body portion having an internal bore configured to receive a valve stem. The internal bore has an internal diameter. A wall has a thickness defined between the internal bore and an exterior surface of the body portion. The body portion further includes an aperture having a diameter selected to avoid atomization of fluid travelling through the aperture. The wall thickness is selected to prevent collapsing of the wall when the valve stem is actuated.

20 Claims, 28 Drawing Sheets

(56) References Cited

U.S. PATENT DOCUMENTS

| | | |
|---|---|---|
| D285,842 S | 9/1986 | Tigert |
| D285,843 S | 9/1986 | Tigert |
| D285,844 S | 9/1986 | Tigert |
| 4,726,519 A | 2/1988 | Muoio |
| 4,889,284 A | 12/1989 | Spector |
| D309,943 S | 8/1990 | Jones et al. |
| D309,996 S | 8/1990 | Gearing |
| D310,021 S | 8/1990 | Anderson |
| D318,746 S | 7/1991 | Austin |
| D326,816 S | 6/1992 | Abrams |
| 5,358,147 A | 10/1994 | Adam et al. |
| D355,712 S | 2/1995 | Barlics |
| D366,803 S | 2/1996 | Hauser et al. |
| 5,636,769 A | 6/1997 | Willingham |
| D380,641 S | 7/1997 | Randle |
| 5,704,259 A | 1/1998 | Riehle |
| 5,765,751 A | 6/1998 | Joshi |
| 5,802,933 A | 9/1998 | Hebert et al. |
| 5,810,253 A | 9/1998 | Ohayon |
| 5,849,264 A | 12/1998 | Bassam et al. |
| 5,862,960 A | 1/1999 | Miller et al. |
| 5,899,382 A | 5/1999 | Hayes et al. |
| D414,060 S | 9/1999 | Talbot-Titley |
| 5,971,369 A | 10/1999 | Neveu et al. |
| 6,104,867 A | 8/2000 | Stathakis et al. |
| 6,131,488 A | 10/2000 | Coonrad |
| D437,040 S | 1/2001 | Soller et al. |
| 6,202,511 B1 | 3/2001 | Murray et al. |
| 6,250,181 B1 | 6/2001 | Coonrad |
| 6,283,337 B1 | 9/2001 | Nakamura et al. |
| 6,338,424 B2 | 1/2002 | Nakamura et al. |
| 6,360,477 B1 | 3/2002 | Flashinski et al. |
| D456,663 S | 5/2002 | Chew |
| 6,412,666 B1 | 7/2002 | Hogan et al. |
| 6,534,079 B1 | 3/2003 | Munagavalasa |
| D474,109 S | 5/2003 | Owens |
| 6,569,387 B1 | 5/2003 | Furner et al. |
| 6,585,016 B1 | 7/2003 | Falligant et al. |
| 6,610,254 B1 | 8/2003 | Furner et al. |
| 6,723,671 B2 | 4/2004 | Zolotarsky et al. |
| D489,642 S | 5/2004 | Brumlow |
| D492,600 S | 7/2004 | Moore |
| D499,796 S | 12/2004 | Walker |
| 6,832,702 B2 | 12/2004 | Garcia |
| D501,248 S | 1/2005 | Chi-Hsiang et al. |
| D502,365 S | 3/2005 | Dretzka |
| D508,594 S | 8/2005 | Snell |
| 6,923,432 B1 | 8/2005 | Martinez |
| 6,957,779 B2 | 10/2005 | Joshi et al. |
| D515,682 S | 2/2006 | LaBlaine |
| 7,066,052 B2 | 6/2006 | Chen |
| 7,134,363 B2 | 11/2006 | Krallman |
| 7,137,534 B2 | 11/2006 | Patel |
| 7,149,417 B2 | 12/2006 | Joshi et al. |
| D538,992 S | 3/2007 | Snell |
| 7,234,648 B2 | 6/2007 | Tepper et al. |
| D550,509 S | 9/2007 | Dretzka |
| D557,073 S | 12/2007 | Snell |
| D561,929 S | 2/2008 | Meeker et al. |
| D565,239 S | 3/2008 | Meeker et al. |
| D565,783 S | 4/2008 | Meeker et al. |
| 7,390,080 B2 | 6/2008 | Silverbrook et al. |
| D573,917 S | 7/2008 | Bigoski |
| D575,899 S | 8/2008 | Meeker et al. |
| D576,759 S | 9/2008 | Meeker et al. |
| D582,724 S | 12/2008 | Dretzka |
| D588,852 S | 3/2009 | Stein |
| 7,549,598 B2 | 6/2009 | Tepper et al. |
| D596,074 S | 7/2009 | Bodum |
| D600,547 S | 9/2009 | Cain |
| 7,600,697 B2 | 10/2009 | Bankers et al. |
| D604,824 S | 11/2009 | Paolazzi et al. |
| D612,976 S | 3/2010 | Meeker et al. |
| D616,139 S | 5/2010 | Meeker et al. |
| D616,594 S | 5/2010 | Meeker et al. |
| D620,569 S | 7/2010 | Hall et al. |
| D625,460 S | 10/2010 | Boissevain |
| 7,861,894 B2 | 1/2011 | Walters et al. |
| 7,887,759 B2 | 2/2011 | Triplett |
| D634,415 S | 3/2011 | Abbondanzio et al. |
| D638,112 S | 5/2011 | Hisey et al. |
| D639,704 S | 6/2011 | Harshman |
| 8,020,733 B2 | 9/2011 | Snodgrass |
| 8,047,099 B2 | 11/2011 | John et al. |
| D651,518 S | 1/2012 | Padain et al. |
| D652,500 S | 1/2012 | Abbondanzio et al. |
| D652,661 S | 1/2012 | Lipfert et al. |
| 8,127,968 B2 | 3/2012 | Yerby et al. |
| D659,886 S | 5/2012 | Wauters |
| D660,940 S | 5/2012 | Flowers et al. |
| D667,151 S | 9/2012 | Arslanian |
| 8,261,634 B2 | 9/2012 | John et al. |
| 8,267,607 B2 | 9/2012 | Harris |
| D672,858 S | 12/2012 | Abbondanzio et al. |
| D673,252 S | 12/2012 | Abbondanzio et al. |
| D680,858 S | 4/2013 | Clark et al. |
| D681,299 S | 4/2013 | Lai |
| 9,334,103 B2 * | 5/2016 | Soliman .............. B65D 83/38 |
| 9,649,400 B2 | 5/2017 | Furner et al. |
| 2005/0275118 A1 | 12/2005 | Chen |
| 2006/0110297 A1 | 5/2006 | D'Amico et al. |
| 2007/0057084 A1 | 3/2007 | Vieira |
| 2007/0140924 A1 | 6/2007 | Hill |
| 2007/0187524 A1 | 8/2007 | Sherwood |
| 2007/0230189 A1 | 10/2007 | Gruenbacher et al. |
| 2007/0295831 A1 | 12/2007 | Ward et al. |
| 2008/0311008 A1 | 12/2008 | Tranzeat |
| 2009/0121041 A1 | 5/2009 | DeFlorian et al. |
| 2010/0038609 A1 | 2/2010 | Chen |
| 2010/0196195 A1 | 8/2010 | Moschel |
| 2010/0322892 A1 | 12/2010 | Burke |
| 2011/0120270 A1 | 5/2011 | Lombardi et al. |
| 2012/0018453 A1 * | 1/2012 | Westphal ............ B65D 83/384 |
| | | 222/162 |
| 2012/0091409 A1 | 4/2012 | Hanlon |
| 2012/0104027 A1 | 5/2012 | Hoppe et al. |
| 2012/0108888 A1 | 5/2012 | Spector |
| 2012/0111966 A1 | 5/2012 | Barlow et al. |
| 2012/0187217 A1 | 7/2012 | Maget et al. |
| 2013/0043284 A1 | 2/2013 | Wegelin et al. |
| 2013/0261349 A1 | 10/2013 | Weiner et al. |

FOREIGN PATENT DOCUMENTS

| | | |
|---|---|---|
| DE | 2540075 A1 | 3/1977 |
| EP | 2233214 A1 | 9/2010 |
| FR | 013047-019 | 9/2001 |
| FR | 013047-023 | 9/2001 |
| FR | 013047-024 | 9/2001 |
| FR | 015603-005 | 12/2001 |
| FR | 096251-002 | 6/2010 |
| GB | 1443314 A | 7/1976 |
| GB | 3001196 | 3/2002 |
| HU | R01936899 | 10/2011 |
| JP | 2000237643 A | 9/2000 |
| JP | 2004091452 A | 3/2004 |
| JP | 2004216269 A | 8/2004 |
| JP | 2014058455 A | 4/2014 |
| WO | 2004096588 | 11/2004 |
| WO | 2005044320 | 5/2005 |
| WO | 2006002395 | 1/2006 |
| WO | 2006105347 | 10/2006 |
| WO | WO2006134353 A1 | 12/2006 |
| WO | 2007062471 | 6/2007 |
| WO | 2008124957 | 10/2008 |
| WO | 2002083043 | 10/2010 |
| WO | 2012059771 | 5/2012 |

OTHER PUBLICATIONS

Japanese Patent Application No. 2015-527680, Office Action dated May 9, 2017 and English Translation, 8 pages.

(56) References Cited

OTHER PUBLICATIONS

European Patent Application No. 13 760 147.2, Office Action dated Apr. 18, 2016, 12 pages.
International Applicaiton No. PCT/US2013/055566, International Search Report and Written Opinion dated Feb. 13, 2014.

* cited by examiner

RETAINING APPARATUS

CROSS REFERENCE TO RELATED APPLICATIONS

Not applicable

REFERENCE REGARDING FEDERALLY SPONSORED RESEARCH OR DEVELOPMENT

Not applicable

SEQUENCE LISTING

Not applicable

BACKGROUND OF THE INVENTION

1. Field of the Invention

The present disclosure generally relates to a retaining apparatus, and more specifically, to an apparatus for retaining an aerosol container within a dispenser housing to emit materials into the surrounding environment.

2. Description of the Background of the Invention

Fluid dispensers are common devices used for the emission of volatile materials into the surrounding environment, such as the release of a pest control agent or the release of a pleasant aroma or odor absorbing agent. Dispensers configured to accept refill containers are an economical way for consumers to re-use a dispenser without having to re-purchase a device. Further, refills afford the user the possibility to change the properties of the fluid that are emitted.

One of the challenges faced by some manufacturers of dispensers and dispenser refills is preventing the use of unapproved or improper refills in the dispensers, e.g., preventing the dispensing of an external use insecticide into an interior environment or dispensing an air freshener when an odor absorber was desired. In many instances the improper spraying of such materials may result in a user being dissatisfied with their experience or the malfunction, destruction, or reduced operability of the dispenser because of the use of an improper material.

Therefore, there is a need for a retaining apparatus that overcomes one or more of the aforementioned drawbacks of dispenser refills. In particular, there is a need for a retaining apparatus that retains and positions an appropriate container for use in a designated dispenser and that prevents the misuse of the container in other applications.

SUMMARY OF THE INVENTION

According to one aspect, a retaining apparatus is configured to couple to a valve stem of an aerosol container and to interface with a dispenser to actuate the valve stem. The apparatus includes a body portion having an internal bore configured to receive a valve stem. The internal bore has an internal diameter. A wall has a thickness defined between the internal bore and an exterior surface of the body portion. The body portion further includes an aperture having a diameter selected to avoid atomization of fluid travelling through the aperture. The wall thickness is selected to prevent collapsing of the wall when the valve stem is actuated.

According to another aspect, a retaining apparatus is configured to couple to a valve stem of an aerosol container and to interface with a dispenser to actuate the valve stem. The apparatus includes a body portion having an internal bore configured to receive a valve stem. The internal bore has an internal diameter and length. The body portion further includes an aperture having a diameter selected to avoid atomization of fluid travelling through the aperture. The valve stem extends at least about 1.7 mm into the internal bore.

According to a further aspect, a retaining apparatus is configured to couple to a valve stem of an aerosol container and to interface with a dispenser to actuate the valve stem. The apparatus includes a body portion defined between an exterior surface and an internal bore configured to receive a valve stem. The body portion further comprises an upper surface and a frustoconical surface or a shoulder between the upper surface and an exterior surface. The frustoconical surface or the shoulder is configured to interface with an angled or rounded surface on a dispenser in order to actuate a valve stem.

BRIEF DESCRIPTION OF THE DRAWINGS

Other aspects and advantages of the present invention will become apparent upon consideration of the following detailed description, wherein similar structures have similar reference numerals.

DETAILED DESCRIPTION

The proper securing of a container into an appropriate dispenser by way of a retention apparatus enhances the user's ability to safely operate a dispenser for emitting a material. For example, a retaining apparatus should preferably only be capable of fitting retention in an identified corresponding dispenser. In many instances the improper spraying of such materials may result in a user being dissatisfied with their experience or the malfunction, destruction, or reduced operability of the dispenser because of the use of an improper material.

Figure 1:
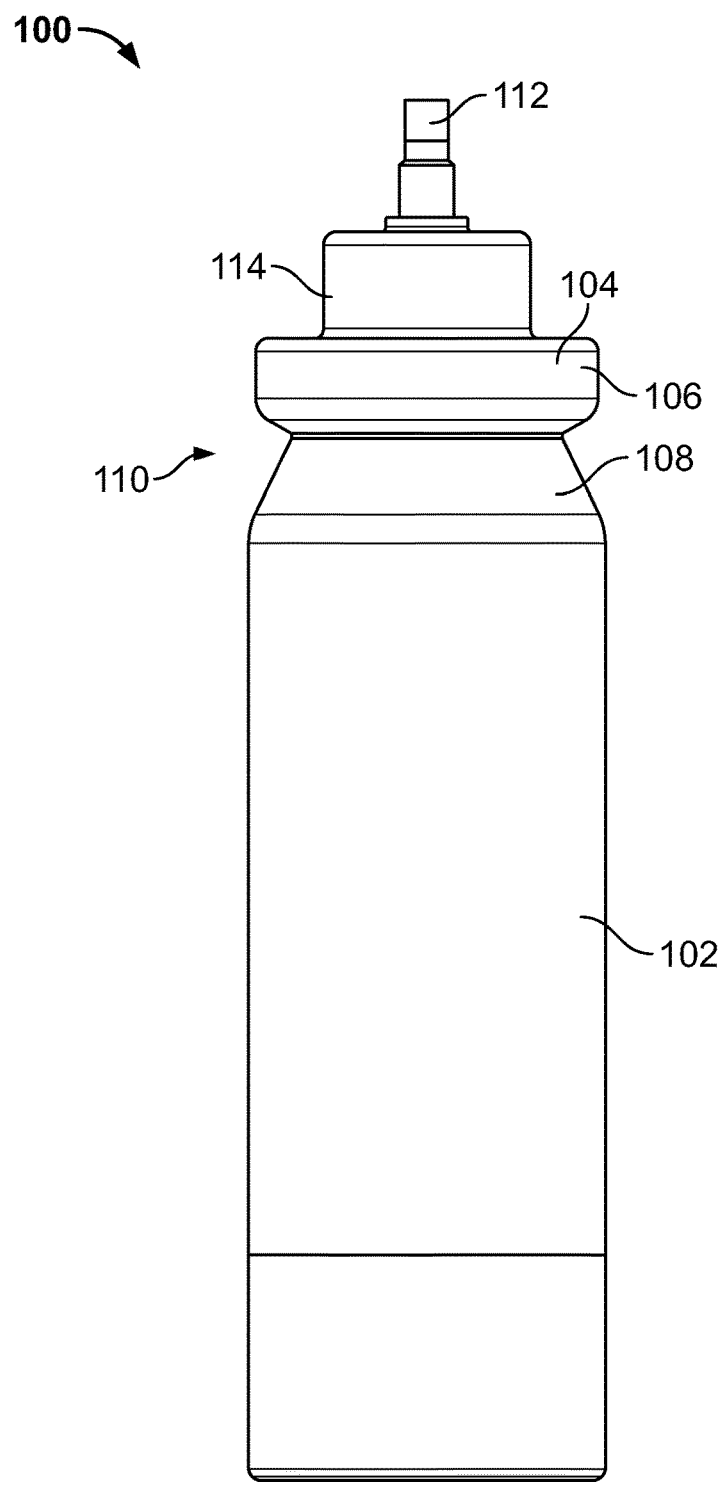
FIG. 1 is an elevational view of an aerosol container.
Figure 2:
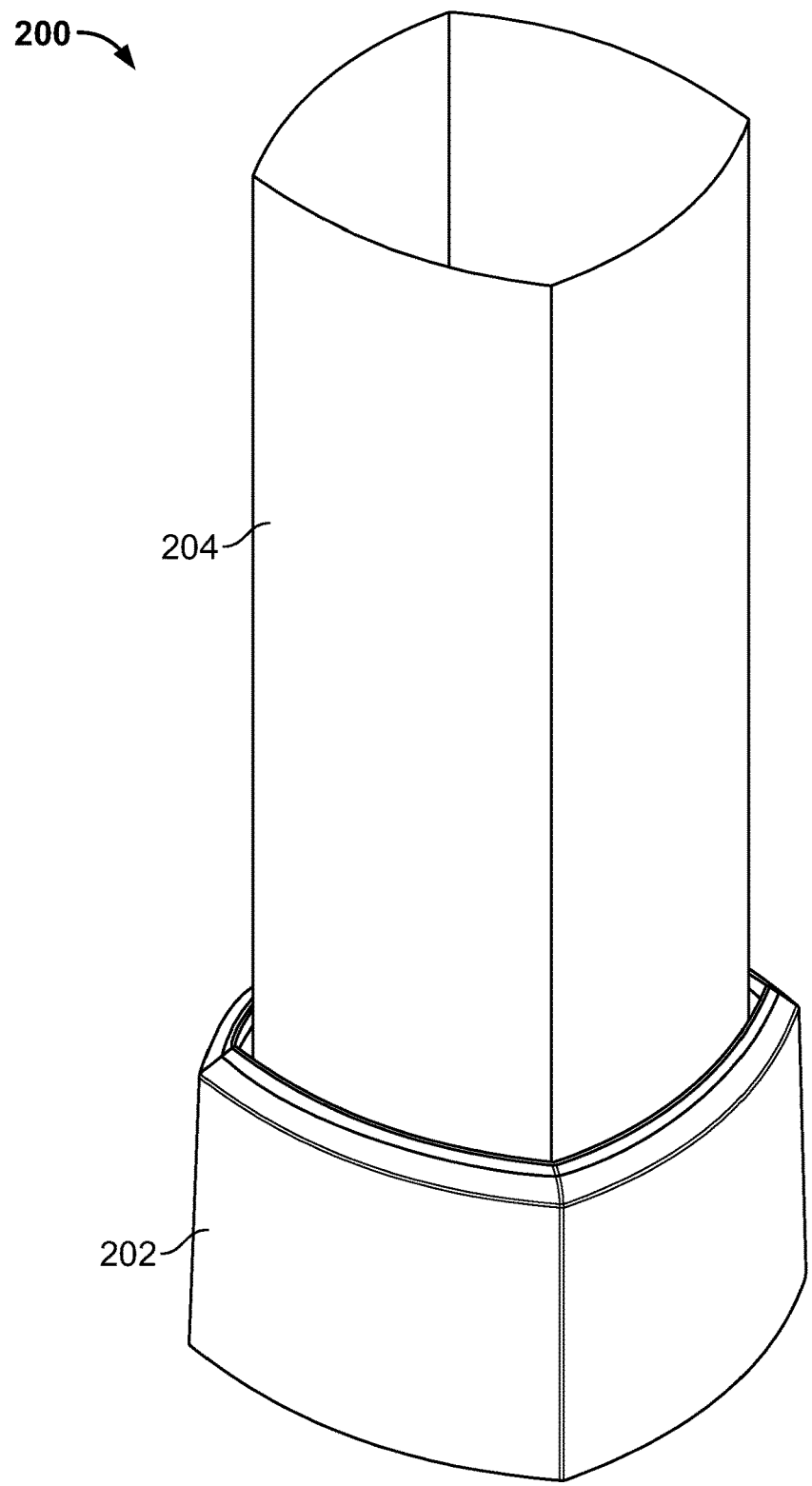
FIG. 2 is an isometric view of a dispenser assembly.

Referring to FIG. 1, an embodiment of a container 100 is depicted. For purposes of the discussion herein, a particular exemplary embodiment will be expounded upon, which utilizes an aerosol-based volatile active-containing composition. However, it should be understood that the disclosed systems, regardless of whether described in connection with an aerosol, a volatile, a composition, etc., are not so bound and may be utilized with any number of liquids or fluids, which may be discharged by one or more of an aerosol system, a compressed gas system, a pump-type sprayer system, or any other means as known to one of ordinary skill.

The aerosol container 100 includes a reservoir or lower portion 102 and a sealing cap or upper portion 104. A lower rim 106 of the sealing cap 104 and an upper tapered portion 108 of the reservoir 102 define a retaining notch 110 that circumscribes the aerosol container 100. A valve stem 112 extends vertically from an upper portion 114 of the sealing cap 104. It is contemplated that in some embodiments that the valve stem 112 may be a vertically actuated valve stem. In other embodiments, the valve stem 112 may be a tilt-actuated valve stem.

The container 100 holds and/or stores a fluid product such as a fragrance, an insecticide, a deodorizer, a fungicide, a bactericide, a sanitizer, a pet barrier, another active volatile or other compound disposed within a carrier liquid (for example, an oil-based and/or water-based carrier), a deodorizing liquid, or the like. For example, the liquid may comprise PLEDGE®, a surface cleaning active, RAID®, a pest control active, OUST®, an air and carpet sanitizer, or GLADE®, a deodorant, all sold by S. C. Johnson and Son, Inc., of Racine, Wis., for household, commercial, or institutional use. The liquid may also comprise other actives, such as sanitizers, air and/or fabric fresheners, cleaners, odor eliminators, mold or mildew inhibitors, insect repellents, and the like, or others that have aromatherapeutic properties. The liquid alternatively comprises any fluid known to those skilled in the art that can be dispensed from the container 100. The container 100 may employ a propellant such as, for example, compressed gas, liquefied petroleum gas (LPG), and/or one or more additional and/or alternative propellants to facilitate dispensing of the fluid product from the container 100.

The dispensers described herein may be used as stand-alone devices, which may be placed on a table, shelf, or other flat surface. Alternatively, the dispensers may be utilized as hand-held devices. The dispensers may be used in an interior room or office and/or outside on a table or other surface. With reference to FIGS. 2-7, one particular embodiment of a dispenser 200 is illustrated that generally includes a base 202 designed to accommodate the container 100 with a flowable medium (not shown). The dispenser 200 further includes a sleeve 204 that extends upwardly from the base 202.

Figure 3:
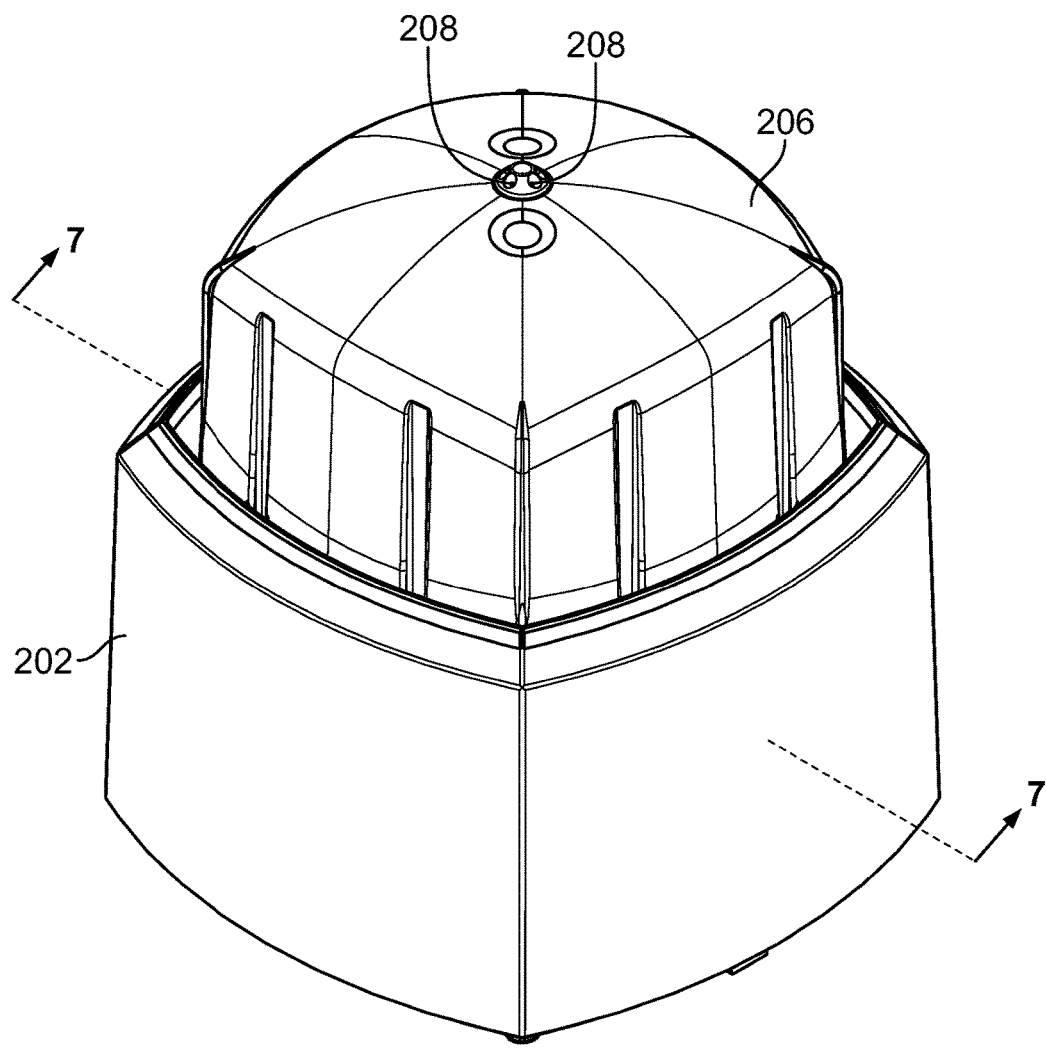
FIG. 3 is an isometric view of a dispenser base of the dispenser assembly of FIG. 2.
Figure 4:
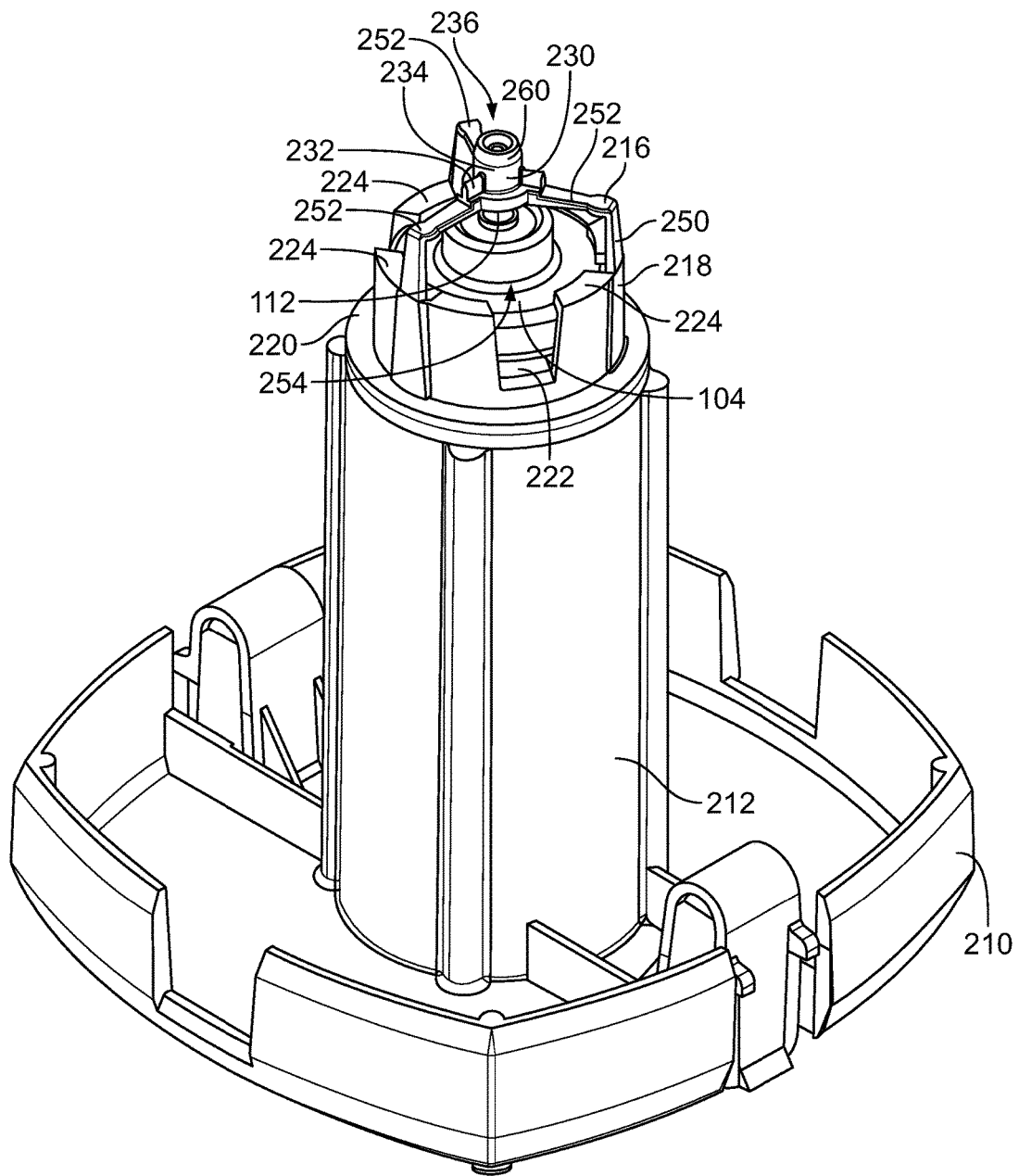
FIG. 4 is an isometric view of a lower housing of the dispenser base of FIG. 3.
Figure 5:
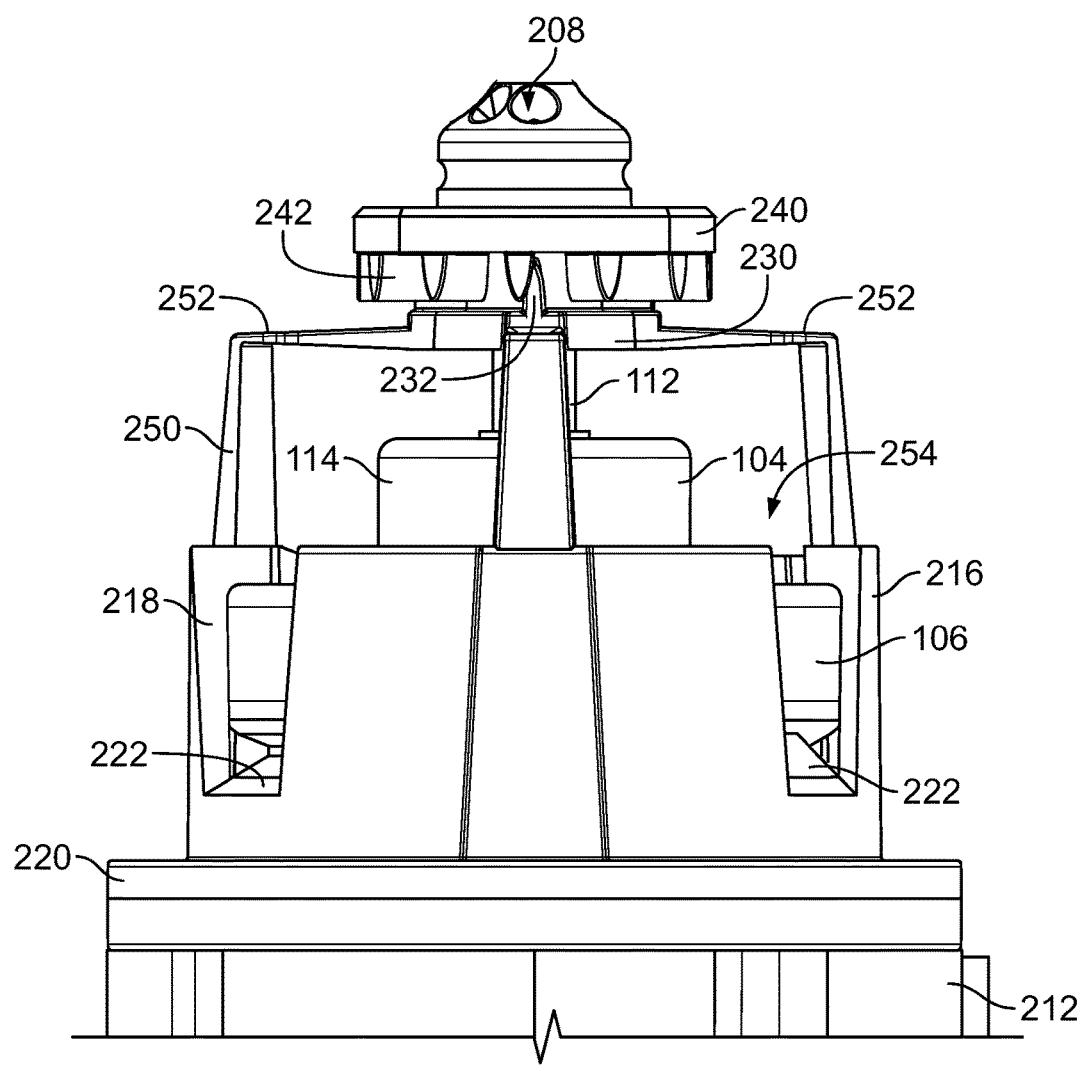
FIG. 5 is a partial, side elevational view of a portion of the lower housing and a portion of an upper housing of the dispenser base of FIG. 3.

Now turning to FIG. 3, the base 202 is depicted without the sleeve 204. The base 202 includes a top cover 206. One or more dispensing apertures 208 may be defined by or provided within the top cover 206. With reference to FIGS. 4 and 5, which illustrate the base 202 without the top cover 206, a base plate 210 is depicted. The base plate 210 includes a sleeve 212, which in the present embodiment is a central cylindrical wall 212. A volume 214 (see FIG. 7) is defined by the central cylindrical wall 212 and receives the lower portion 102 of the aerosol container 100 when the container 100 is mounted in the dispenser 200.

Figure 7:
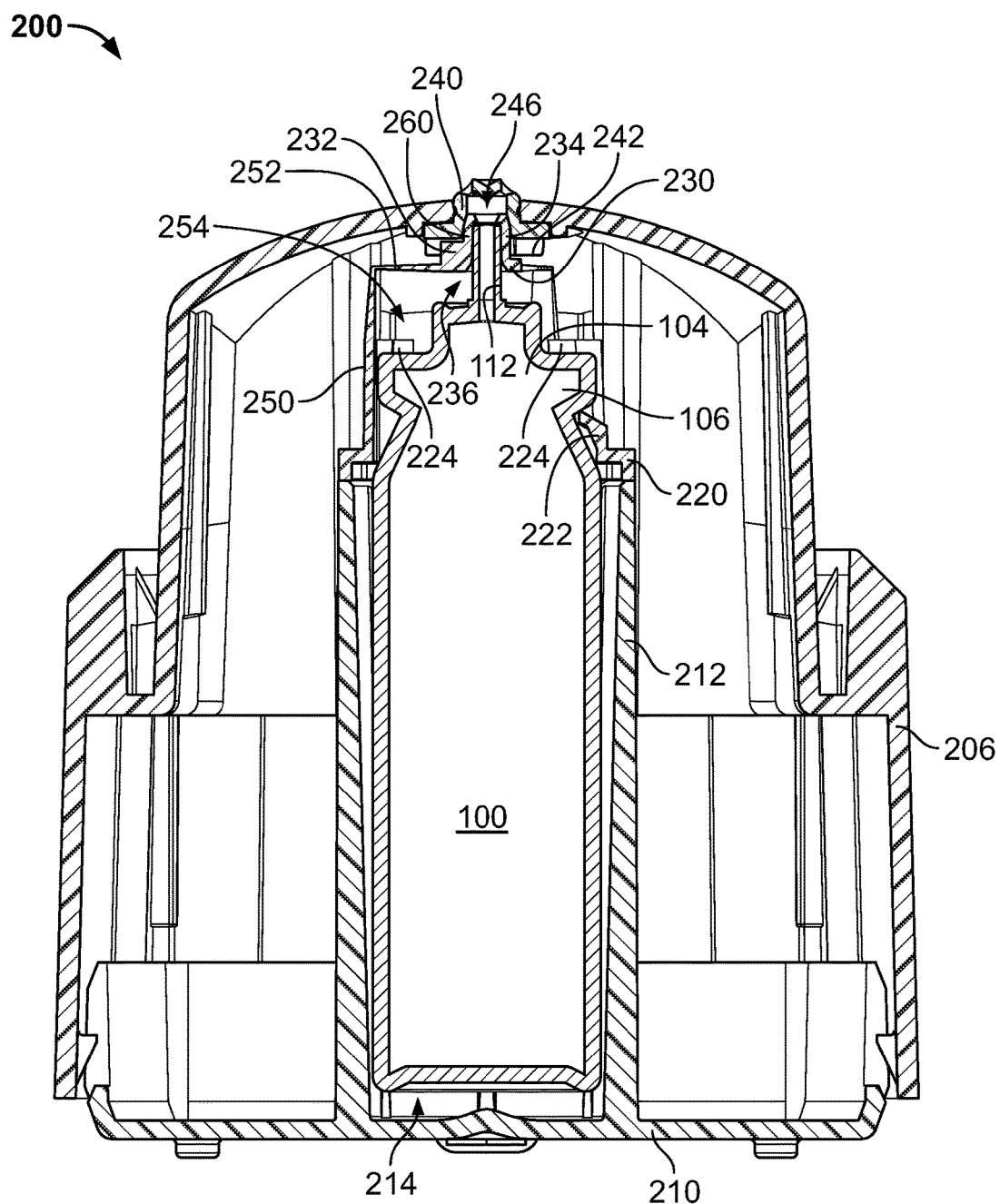
FIG. 7 is a cross-sectional view of the dispenser base of FIG. 3 taken along the line 7-7 thereof with portions of the container removed for purposes of clarity.
Figure 8:
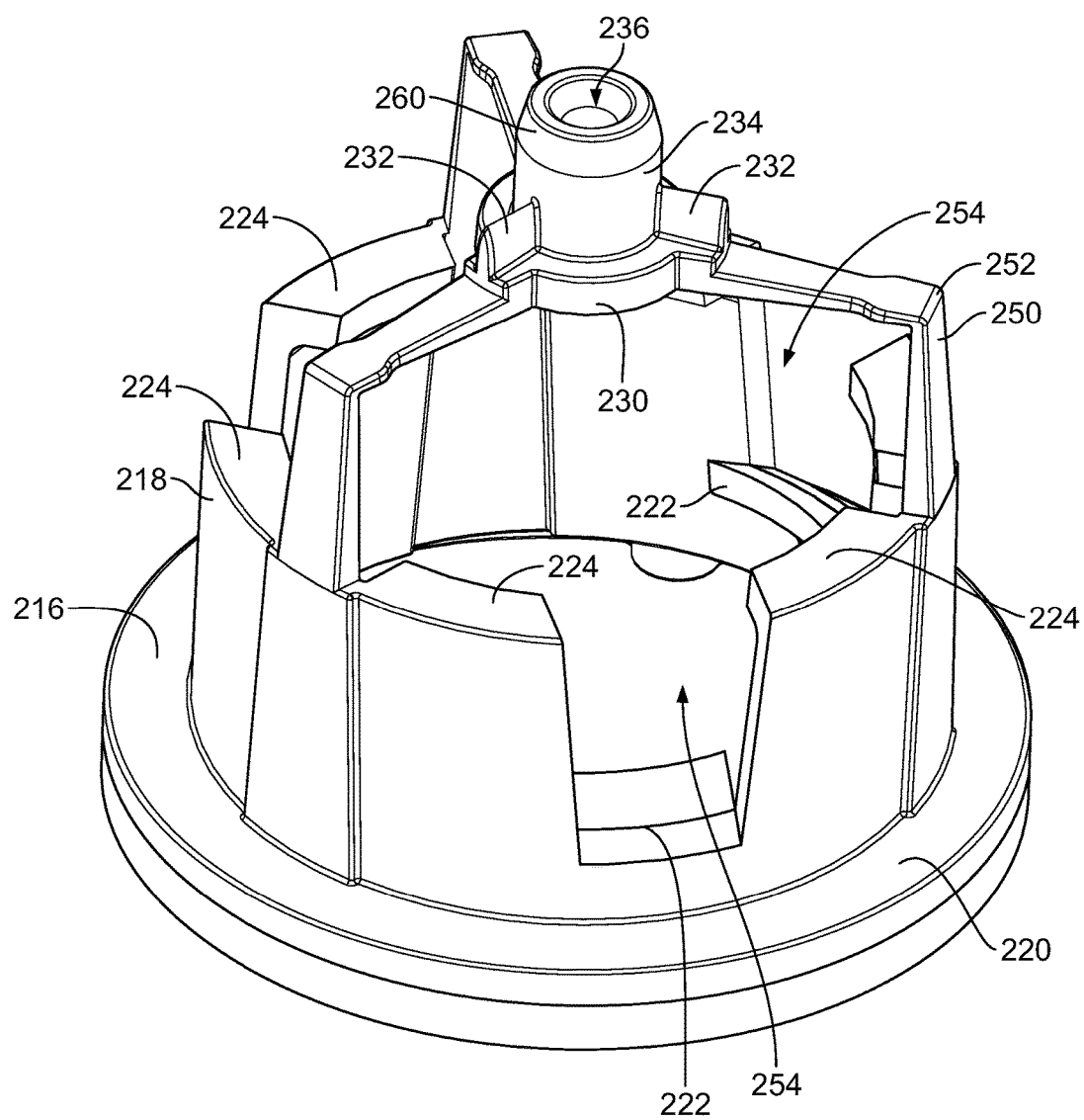
FIG. 8. is an isometric view of one embodiment of a retaining apparatus.
Figure 9:
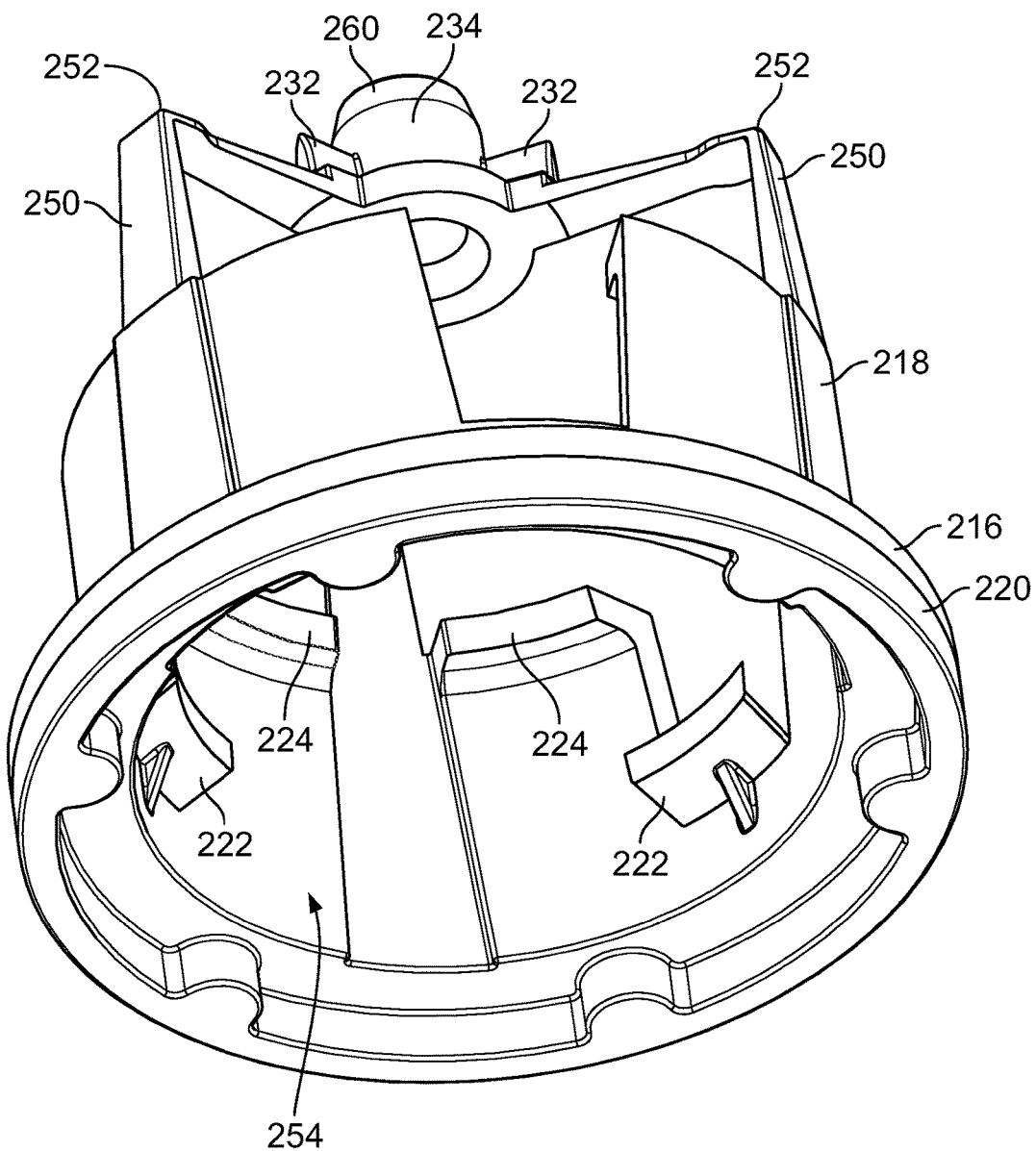
FIG. 9 is another isometric view of the retaining apparatus of FIG. 8.
Figure 10:
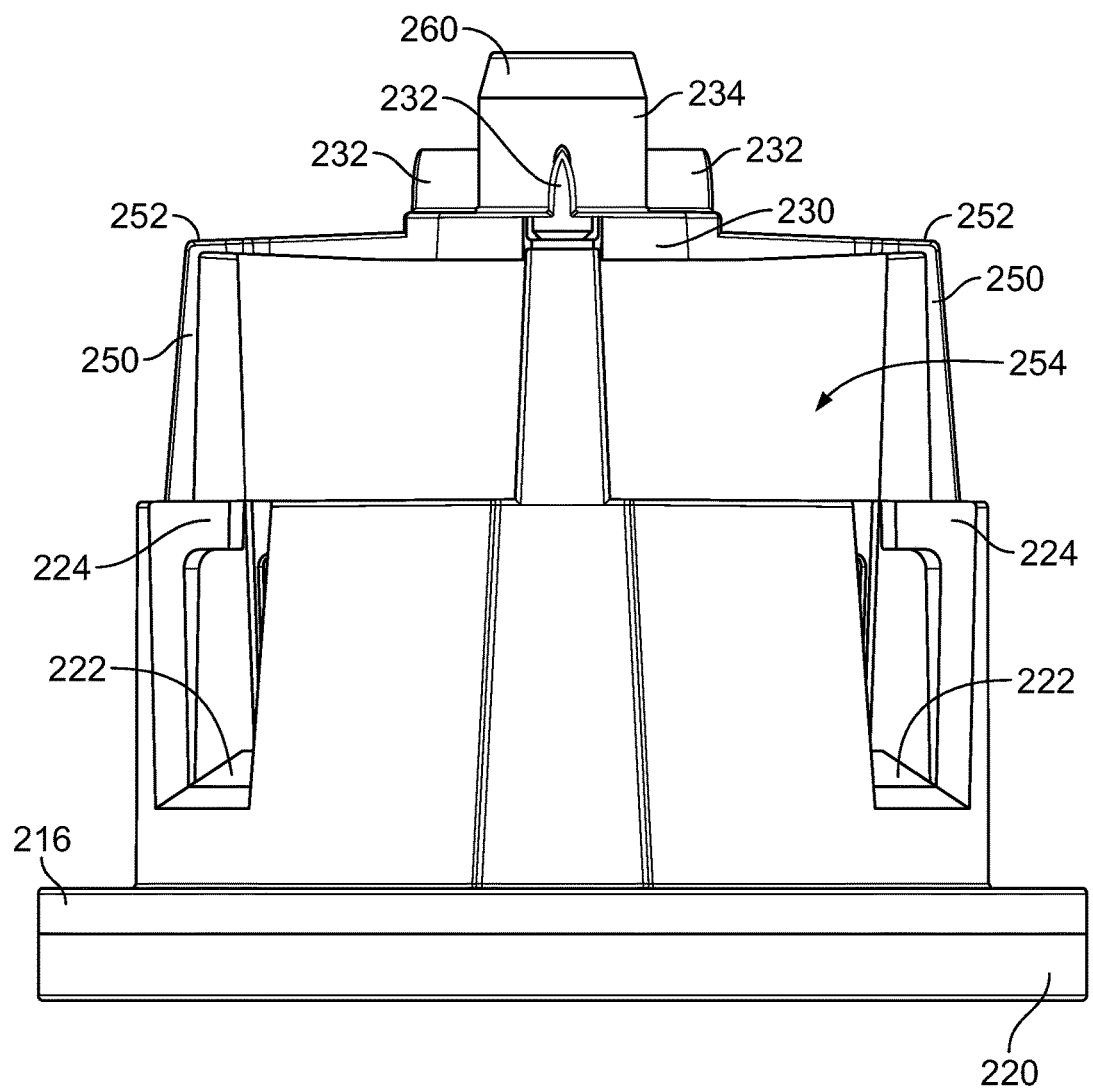
FIG. 10 is a side elevational view of the retaining apparatus of FIG. 8.
Figure 11:
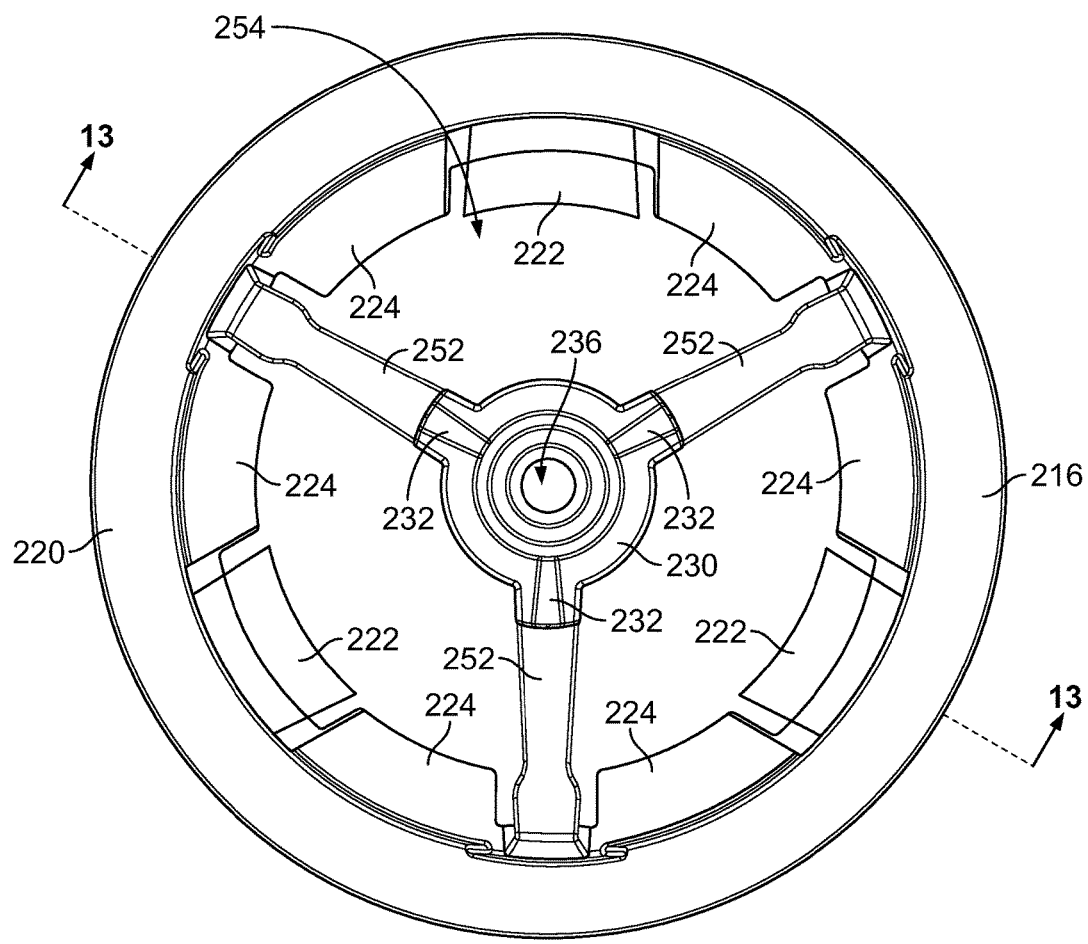
FIG. 11 is a top plan view of the retaining apparatus of FIG. 8.
Figure 12:
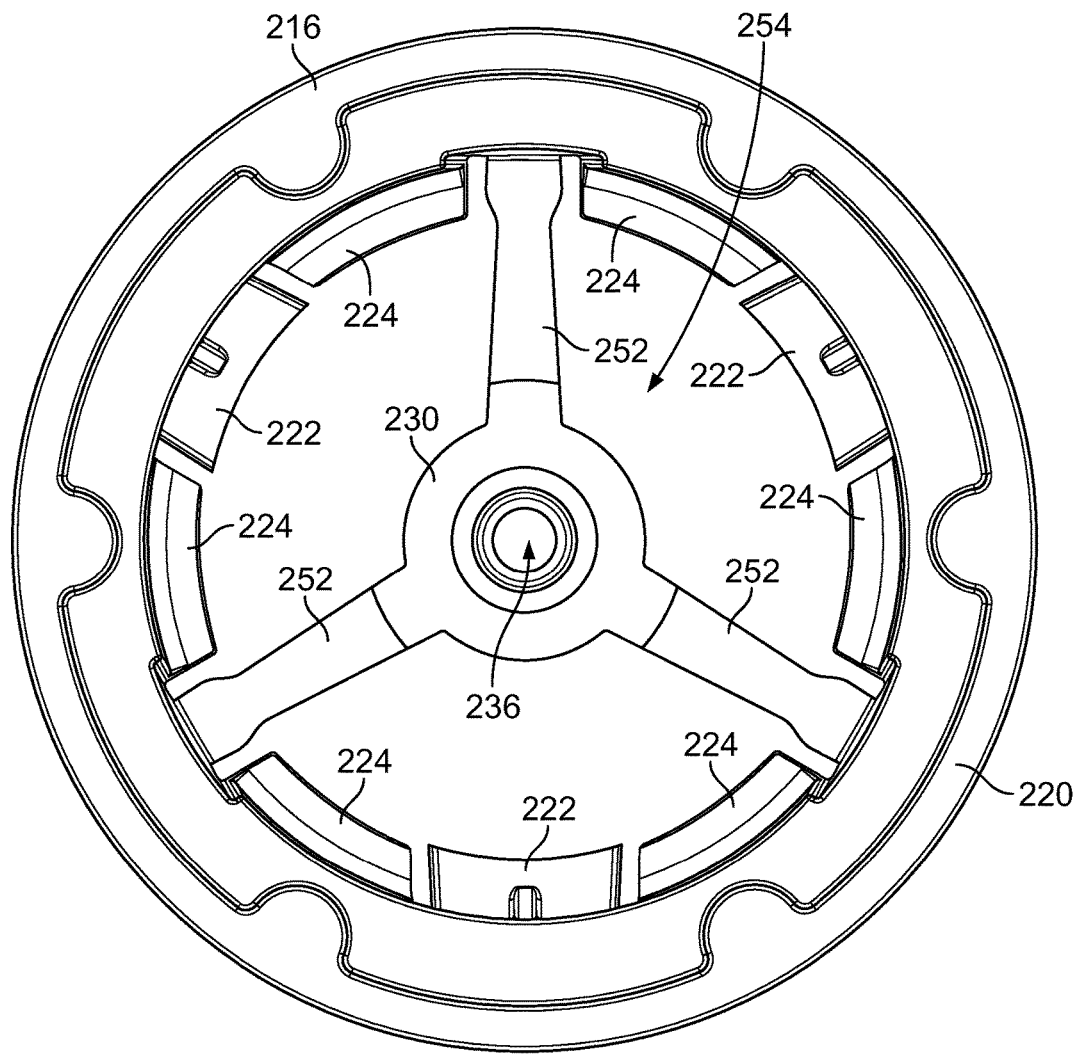
FIG. 12 is a bottom elevational view of the retaining apparatus of FIG. 8.
Figure 14:
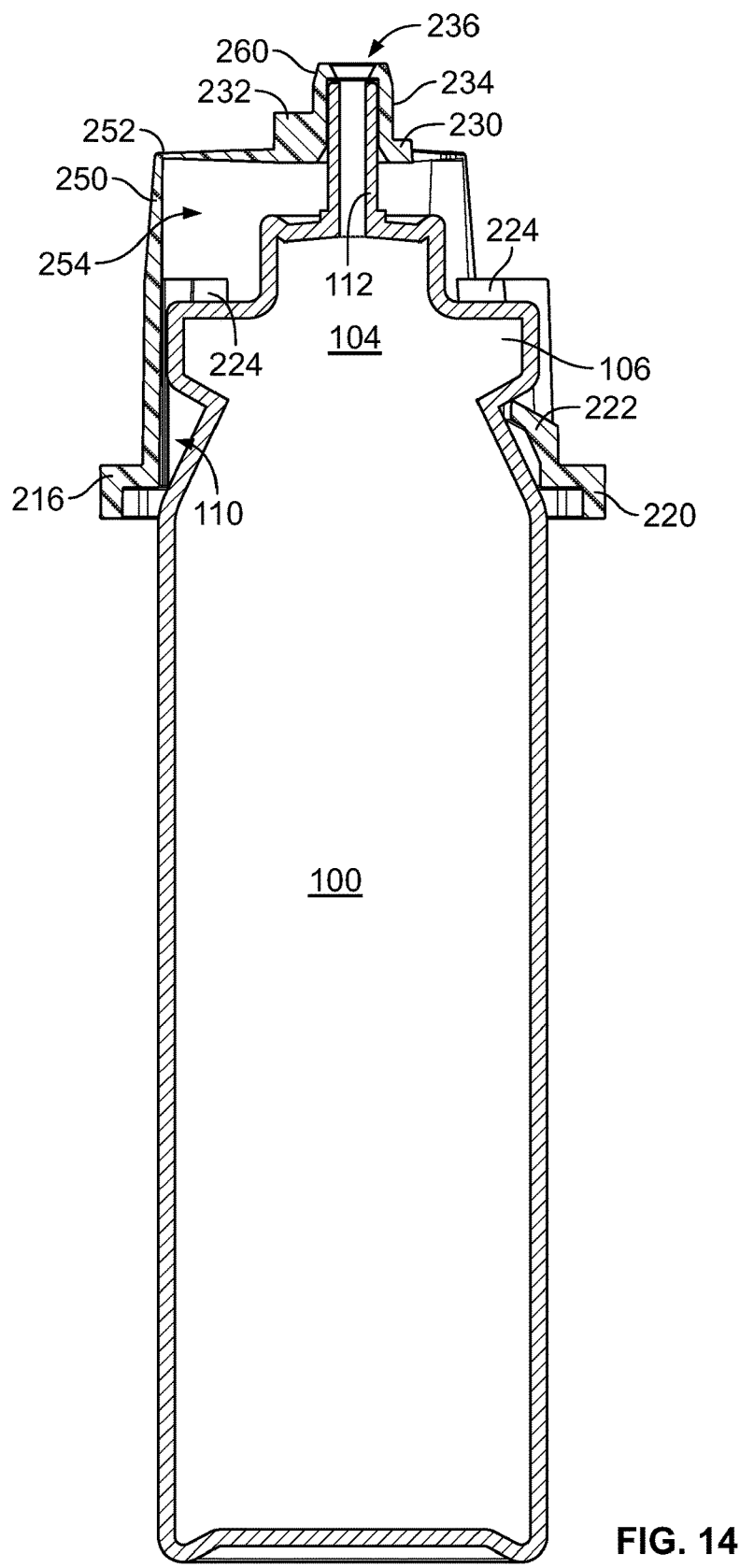
FIG. 14 is a cross-sectional view of the retaining apparatus of FIG. 13 mounted on the aerosol container of FIG. 1 with portions of the container removed for purposes of clarity.

Referring to FIGS. 4, 5, 7 and 14, a first embodiment of a retaining apparatus 216 is shown retaining the aerosol container 100. The retaining apparatus 216 includes a lower portion 218 with a flange 220 extending radially outward therefrom. In the present embodiment, the flange 220 rests on an upper end of the cylindrical wall 212 to hold the container above the base plate 210. Retaining tabs 222 extend radially inward from the lower portion 218 of the retaining apparatus 216. The retaining tabs 222 are configured to hold the aerosol container 100 within the retaining apparatus 216 by snapping into the retaining notch 110, as best seen in FIG. 5. The retaining apparatus 216 and the sealing cap 104 are dimensioned so that the lower rim 106 of the sealing cap 104 is immovably retained between the retaining tabs 222 and an upper lip 224 extending inwardly over the lower rim 106, as best seen in FIGS. 7 and 14.

Returning to FIGS. 4 and 7-14, the retaining apparatus 216 also includes an upper portion 230. A plurality of upwardly facing teeth 232 are circumferentially disposed around a central tube 234 that defines a discharge bore 236 with an axial portion having a length in an axial direction and a tapered surface adjacent the axial portion, the tapered surface having a length in the axial direction smaller than the axial portion length.

Figure 6:
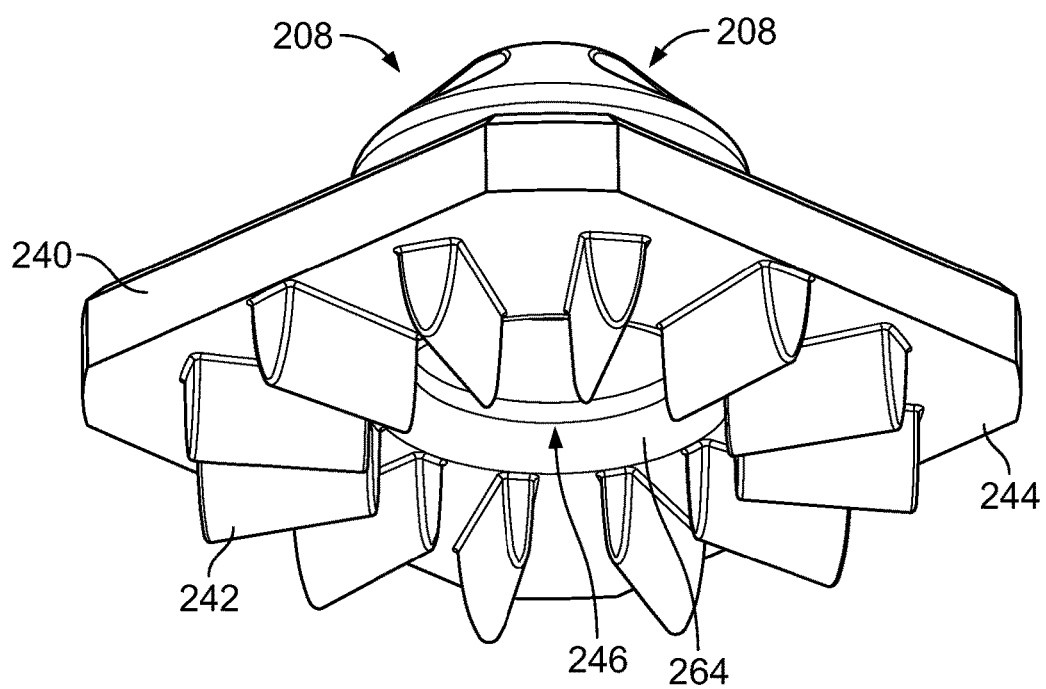
FIG. 6 is an isometric view of a portion of an upper housing of the dispenser base of FIG. 3.

Now turning to FIGS. 5 and 6, a discharge portion 240 of the top cover 206 is depicted. The discharge portion 240 may be disposed on an underside of the top cover 206 in order for the discharge portion 240 to interface with the retaining apparatus 216.

A plurality of downward facing teeth 242 depend from a bottom surface 244 of the discharge portion 240 and are disposed circumferentially around a central dispensing bore 246. It is contemplated that the discharge portion 240 of the top cover 206 may be a separate piece as depicted here. In such a scenario, the discharge portion 240 may be press fit into a receiving aperture (not shown) of the top cover 206 or attached by any other means as would be known by one of ordinarily skill. In other embodiments, the discharge portion 240 may be integrally formed with the top cover 206 or attached in some other manner.

Turning again to FIG. 5, the retaining apparatus 216 is depicted with the discharge portion 240 assembled such that the upward facing teeth 232 are positioned between respective pairs of the downward facing teeth 242. In one aspect, the upward facing teeth 232 are sized to form an interference fit between the respective pairs of downward facing teeth 242. In another aspect, and as shown in the figures, the upward facing teeth 232 are sized to provide circumferential and/or longitudinal clearance between the respective pairs of downward facing teeth 242. For example, the tips of the upward facing teeth 232 and a bottom surface 244 of the discharge portion 236 may be distanced from one another. Regardless of whether the teeth 232, 242 are in contact, one or both of the upward facing teeth 232 and the downward facing teeth 242 may have ramped surfaces to facilitate engagement between the teeth.

The retaining apparatus 216 includes a bridge portion 250 that includes a plurality of resilient arms 252 coupling the upper portion 230 to the lower portion 218. As seen in FIG. 4, the upward facing teeth 232 are circumferentially aligned with a respective plurality of resilient arms 252. The lower portion 218, bridge portion 250, and upper portion 230 define a cavity 254 configured to receive and retain the sealing cap or upper portion 104 of an aerosol container 100.

As best seen in FIG. 7, the valve stem 112 of the aerosol container 100 is positioned within the discharge bore 236 of the central tube 234 of the retaining apparatus 216 upon insertion of the container 100 therein. When the top cover 206 including the discharge portion 240 is assembled over the base plate 210, the central tube 234 of the retaining apparatus 216 is received within the central dispensing bore 246 of the discharge portion 240.

With continued reference to FIG. 7, it has been contemplated that when a user grasps the top cover 206 and presses downward, the force is transferred from the top cover 206 to the central discharge portion 240 and subsequently on to the upper portion 230 of the retaining apparatus 216. The flange 220 of the retaining apparatus 216 prevents the container 100 from moving during the actuation of the dispenser 200. Additionally, the resilient arms 252 of the bridge section 250 deform, thereby allowing the downward force to translate to the vertical movement of the valve stem 112 within the central tube 234 of the retaining apparatus 216. This, in turn, opens a valve within a valve assembly (not shown) of the aerosol container 100 to allow for the dispensing of the flowable medium contained therein. Upon release of the top cover 206, the spring force of the valve assembly (not shown) returns the dispenser to the pre-actuated position. The resilient arms 252 of the bridge section 250 also return to their pre-actuated position and, in some embodiments, may assist in returning the dispenser to the pre-actuated position. It is further anticipated that a resilient member(s) or other means within the dispenser may assist or solely cause the dispenser to regain a pre-actuated position. In this state, the dispenser 200 is ready for use and the emission of material.

While the embodiment depicted in FIG. 7 includes a container 100 that extends almost completely to the base plate 210, it is contemplated that in some embodiments, the container 100 may extend the entire length of the wall 212 to the base plate 210. Further, in other embodiments the container 100 may be significantly shorter than the central cylindrical wall so as to be raised above the base plate 210.

It is contemplated that one or more aspects of the upper portion 230 of the retaining apparatus 216 overcomes the drawbacks to refill containers described above. First, the upward facing teeth 232 can serve multiple purposes. The length of the central tube 234 to the teeth 232 may provide a structural relationship such that a seal is impossible to form between the central tube 234 and an improper dispenser. Further, the appearance in general of the upward facing teeth 232 and the retaining apparatus 216 may serve as a visual indicator to a user about the purpose of the refill. Also, the enlarged diameter of the central tube 234 of the retaining apparatus 216 in comparison to a diameter of the valve stem 112 of the container 100 may also prevent different containers from establishing fluid communication with unintended dispensers. As configured in the present embodiment, any dispenser that receives the retaining apparatus 216 will need a receptacle that is configured to receive the central tube 234, which has a larger diameter than the valve stem 112.

Figure 13:
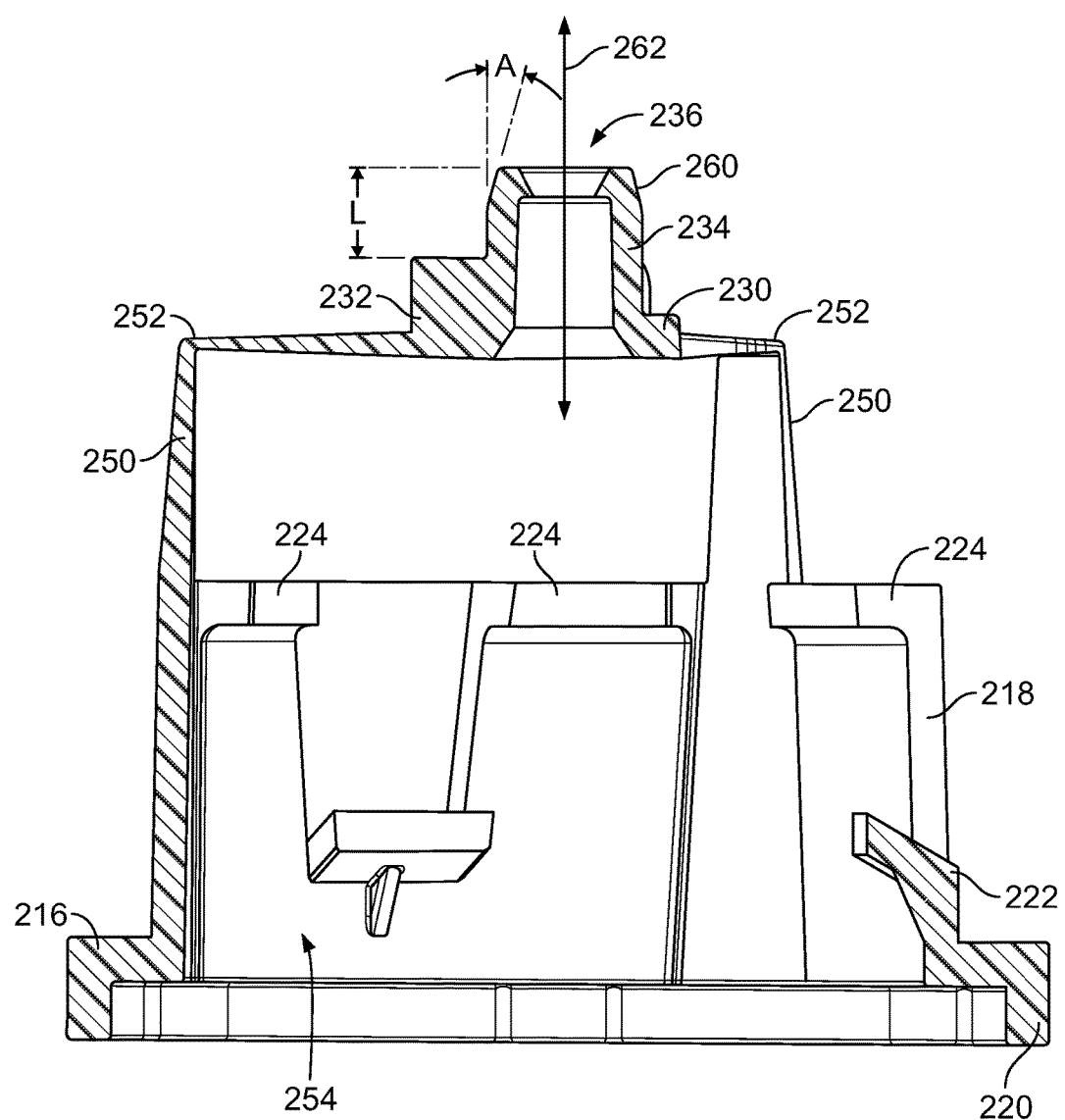
FIG. 13 is a cross-sectional view of the retaining apparatus of FIG. 8 taken along the line 13-13 of FIG. 11.

Now referring to FIG. 13, the central tube 234 may include an upper tapered or angled section 260, thereby forming a frustoconical shoulder depending downward from an upper edge of the central tube 234. The angled section 260 is angled inward at an angle A toward a central axis 262 of the retaining apparatus 216. The angled section 260 is configured to form a seal with a tapered or angled portion 264 (see FIG. 6) disposed around the circumference of the central dispensing bore 246 of the discharge portion 240 of the base. As an alternative to the frustoconical surface shown in FIG. 13, the angled section 260 (and/or the angled portion 264 of FIG. 6) may be replaced with a curved profile (not shown) to enhance the sealing relationship. The curved profiles in some embodiments may have a radius of curvature of about 0.5 millimeters (mm). In other embodiments the radius of curvature R is between about 0.4 mm and about 1.0 mm. In yet other embodiments the radius of curvature R is between about 0.2 mm and about 1.5 mm. In some embodiments the angle A is about 15° (degrees). In certain embodiments the angle A is between about 12° and about 18°. In other embodiments the angle A is between about 10° and about 20°. In a particular embodiment the angle is at least about 10°. Although shown and described in connection with the embodiments of FIGS. 4-15, the central tube 234 in each of the following embodiments described herein may include the same or a similar angled portion or rounded portion.

Figure 15:
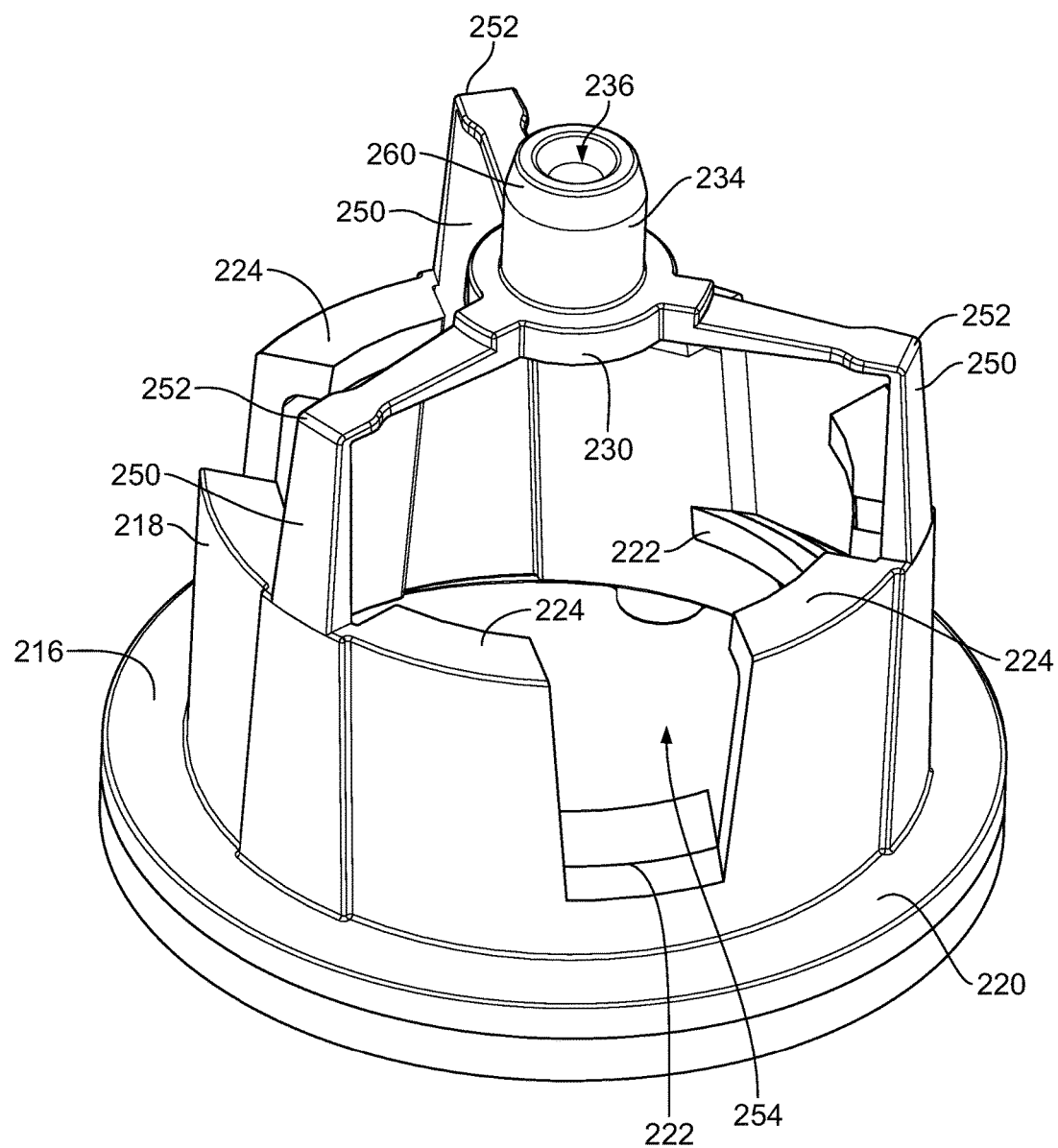
FIG. 15 is an isometric view of another embodiment of a retaining apparatus.

With reference still to FIG. 13, and in general to all embodiments that include teeth 232, the central tube 234 may extend a length L upwardly beyond the uppermost edges of the plurality of upward facing teeth 232. It is contemplated that in some embodiments the length L is about 2.6 millimeters (mm). In other embodiments the length L is between about 1 mm and about 3 mm. In still other embodiments the length L is between about 2 mm and about 3 mm. The length L of the central tube 234 above the plurality of upward facing teeth 232, or in an embodiment with no upward facing teeth 232 the entire length of the conduit, can be configured so as to prevent the angled section 260 from forming a seal in improper devices. As discussed previously, by making the distance L shorter than the extent a valve stem 112 is traditionally inserted into a device, the functionality of such containers 100 that do not utilize the retaining apparatus 216 is reduced. Another embodiment of the retaining apparatus 216 is depicted in FIG. 15, that is structurally and operationally identical to the embodiment depicted in FIGS. 4-15 except that there are no upward facing teeth 232.

Figure 21:
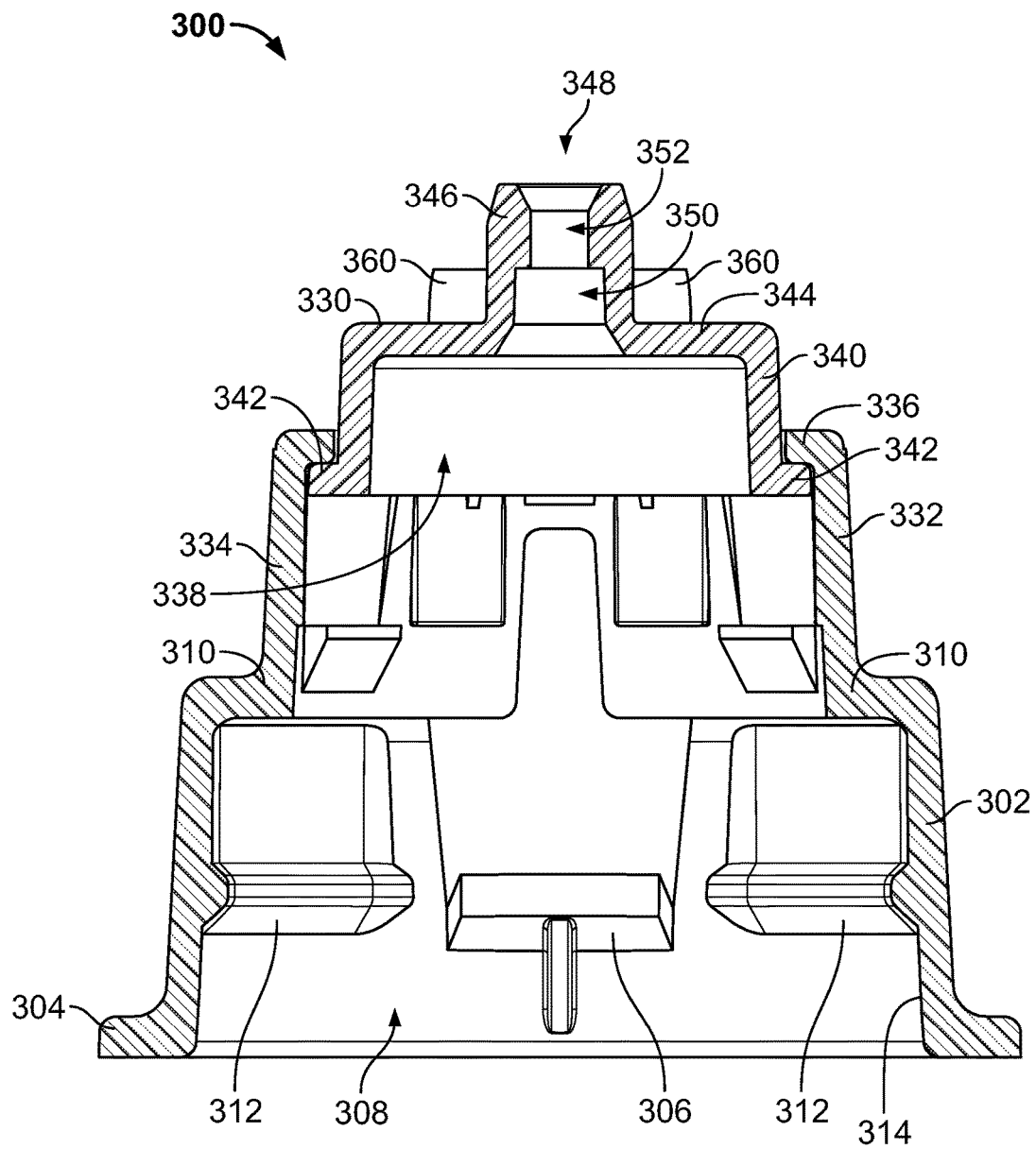
FIG. 21 is a cross-sectional view of the retaining apparatus of FIG. 16 taken along the line 21-21 thereof of FIG. 19.
Figure 22:
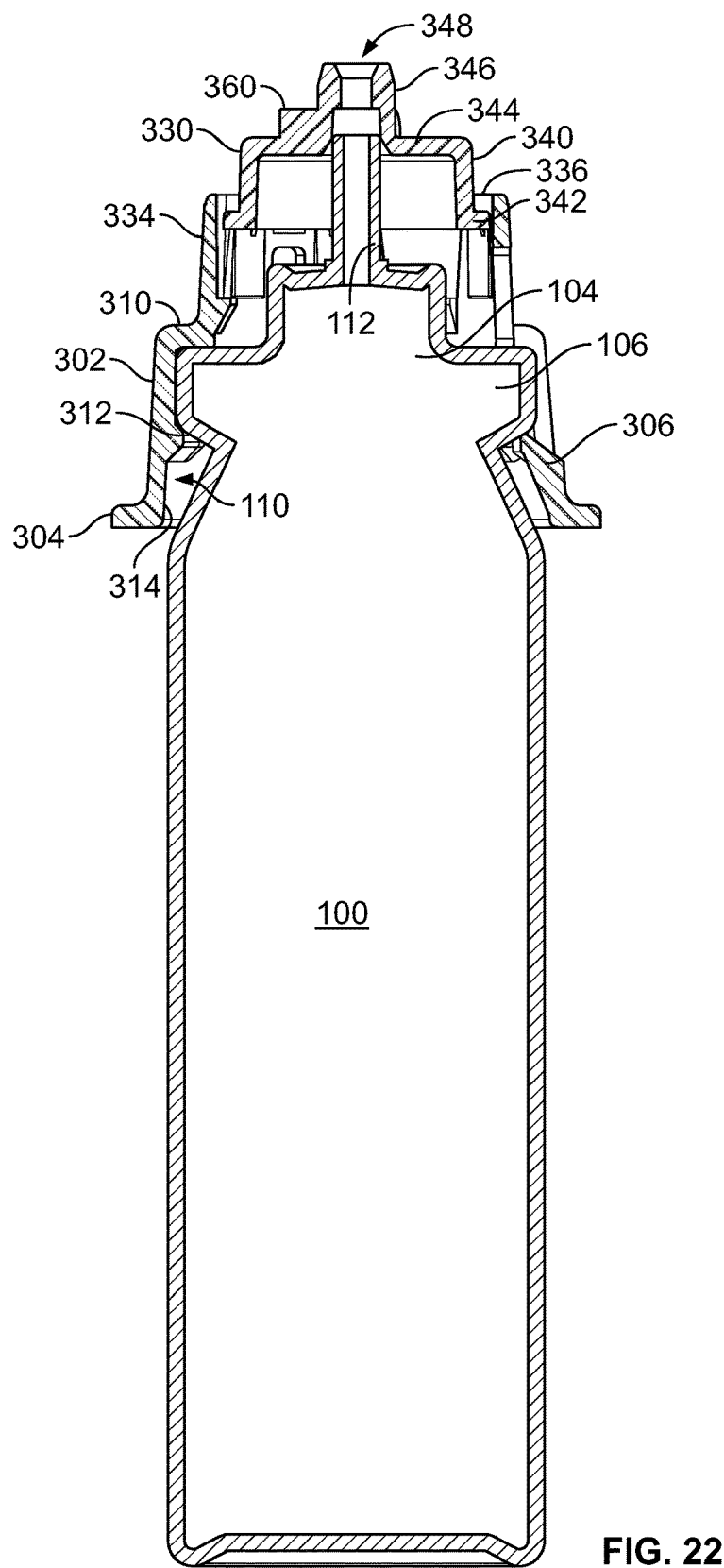
FIG. 22 is a cross-sectional view of the retaining apparatus of FIG. 21 taken along the line 22-22 of FIG. 19 and further mounted on the aerosol container of FIG. 1 with portions of the container removed for purposes of clarity.

Referring now to FIGS. 16-23, a second embodiment of a retaining apparatus 300 is depicted. The retaining apparatus 300 comprises a lower portion 302 that includes a flange 304 extending circumferentially therefrom. The lower portion 302 also includes inward facing retaining tabs 306. A container 100 is retained within the retaining apparatus 300 by the retaining tabs 306 snapping into place in the retaining notch 110 of the container 100 (as shown in FIG. 22). The lower portion 302 defines an interior volume 308 (see FIG. 17). The lower portion 314 includes a lip 310 extending into the interior volume 308 configured to abut the lower rim 106 of the sealing cap 104. Thus, when a container 100 is inserted into the retaining apparatus 300, the lower rim 106 of the sealing cap 104 is retained between the retaining tabs 306 and the lip 310 of the lower portion 302 (see FIG. 22). The lower portion 302 includes rounded protrusions 312 that extend inward from an interior surface 314 of the lower portion 302 (see FIGS. 17 and 21). The rounded protrusions 312 are configured to support the lower rim 106 of the container 100 by extending into the retaining notch 110 (see FIG. 22).

The embodiments depicted in FIGS. 16-23 include a separate upper portion 330. As best seen in FIG. 21, the upper potion 330 is slidably or telescopically disposed within a bridge section 332 of the lower portion 302.

Figure 16:
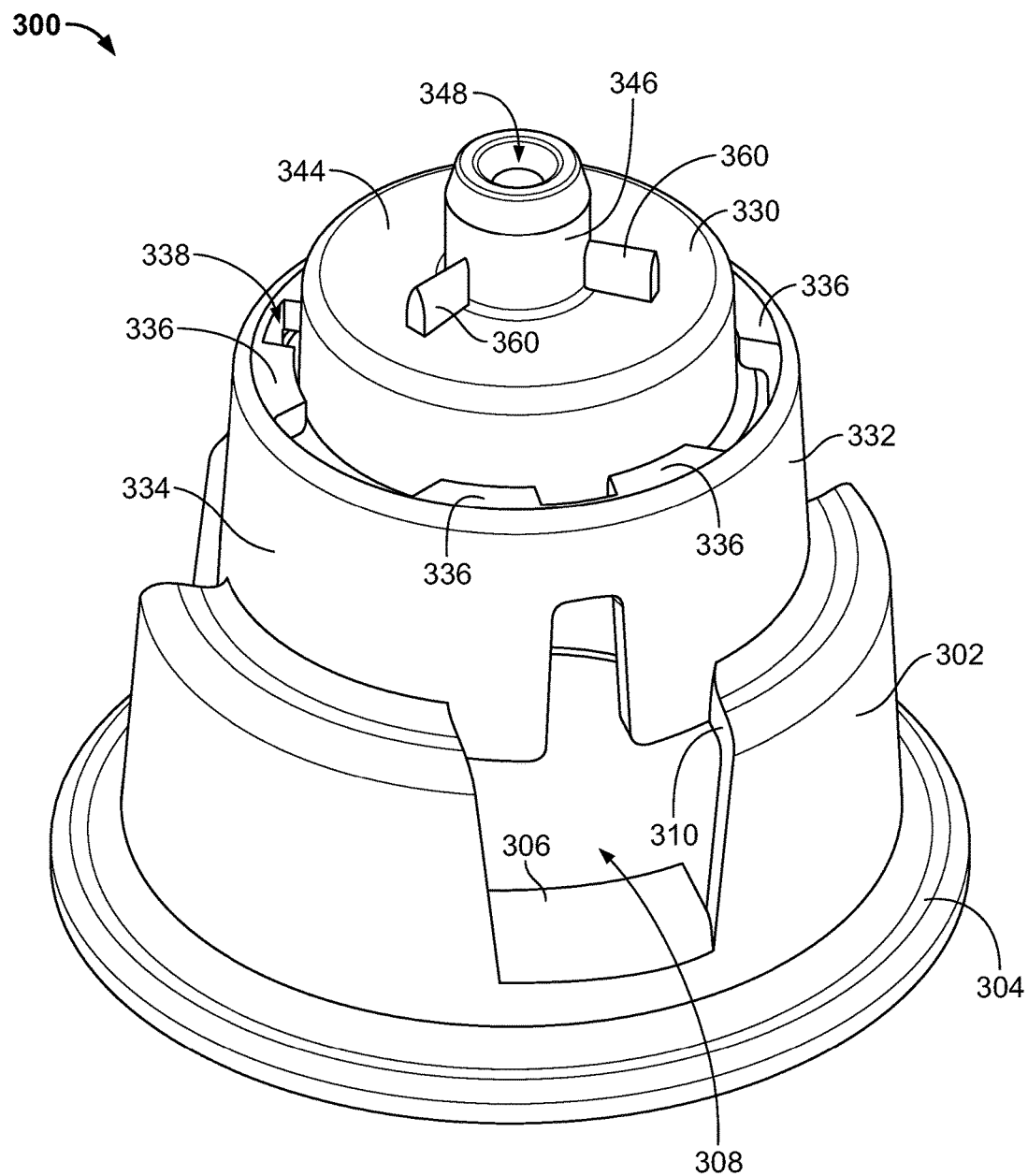
FIG. 16 is an isometric view of still another embodiment of a retaining apparatus.
Figure 17:
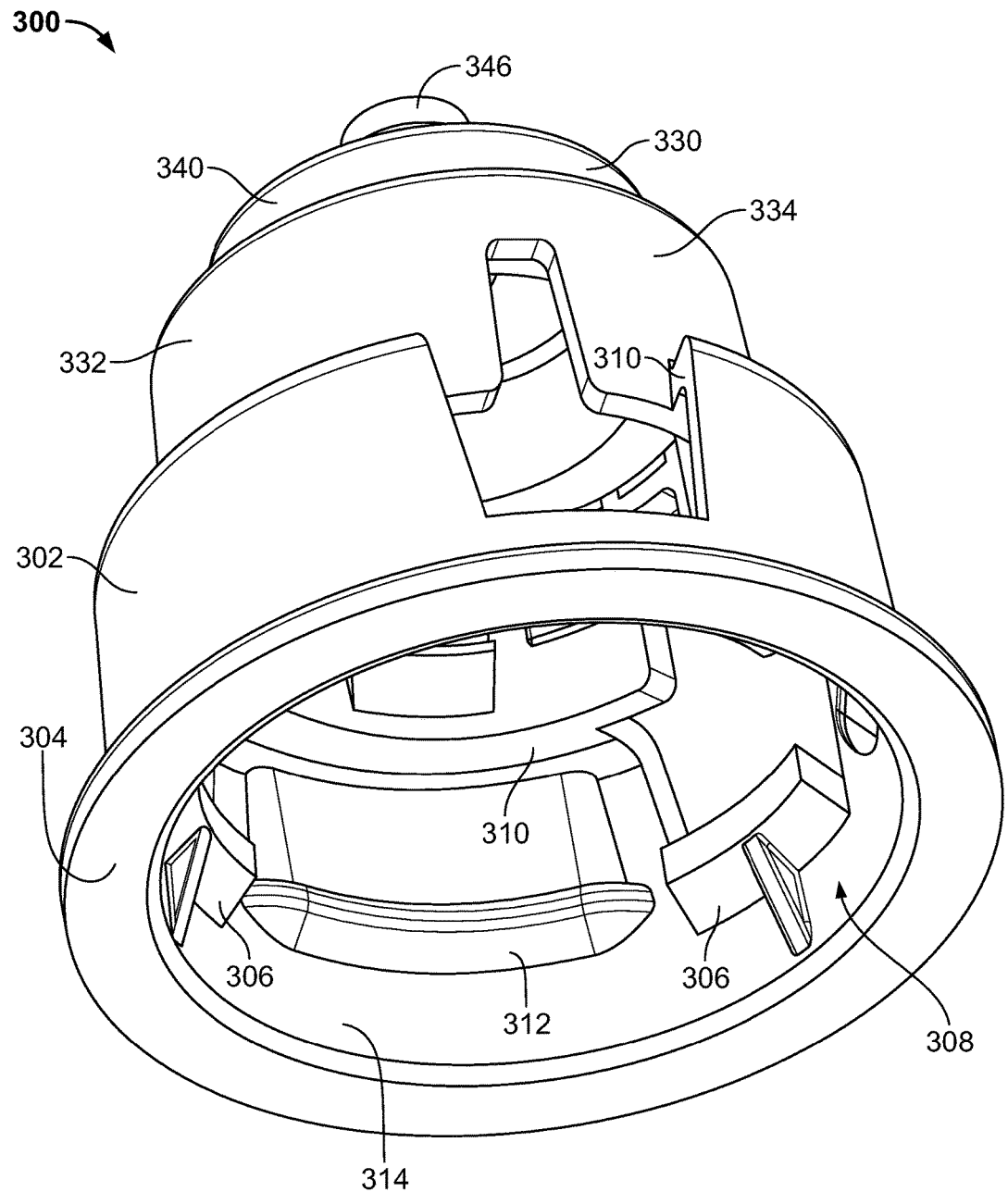
FIG. 17 is another isometric view of the retaining apparatus of FIG. 16.
Figure 18:
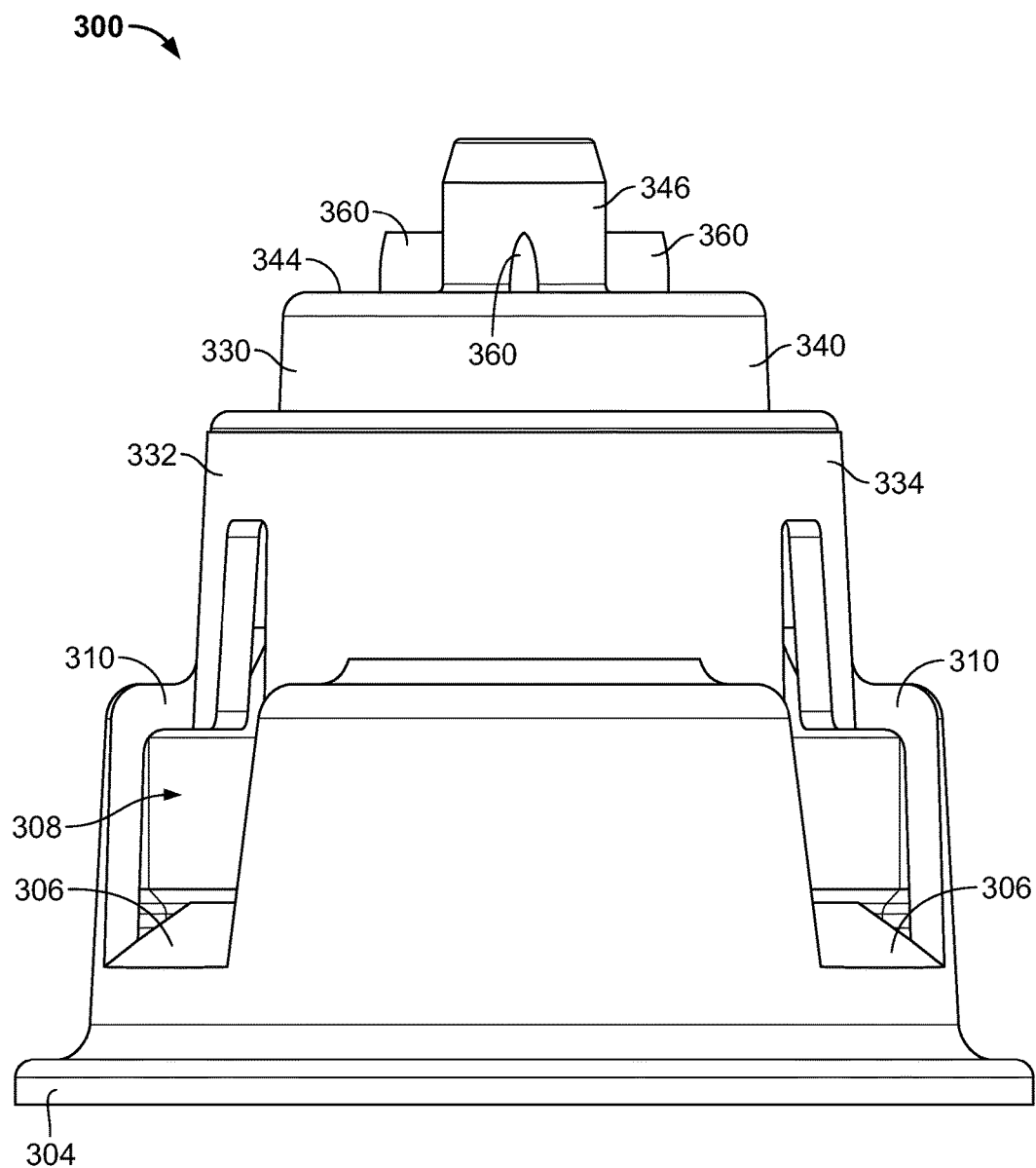
FIG. 18 is a side elevational view of the retaining apparatus of FIG. 16.
Figure 19:
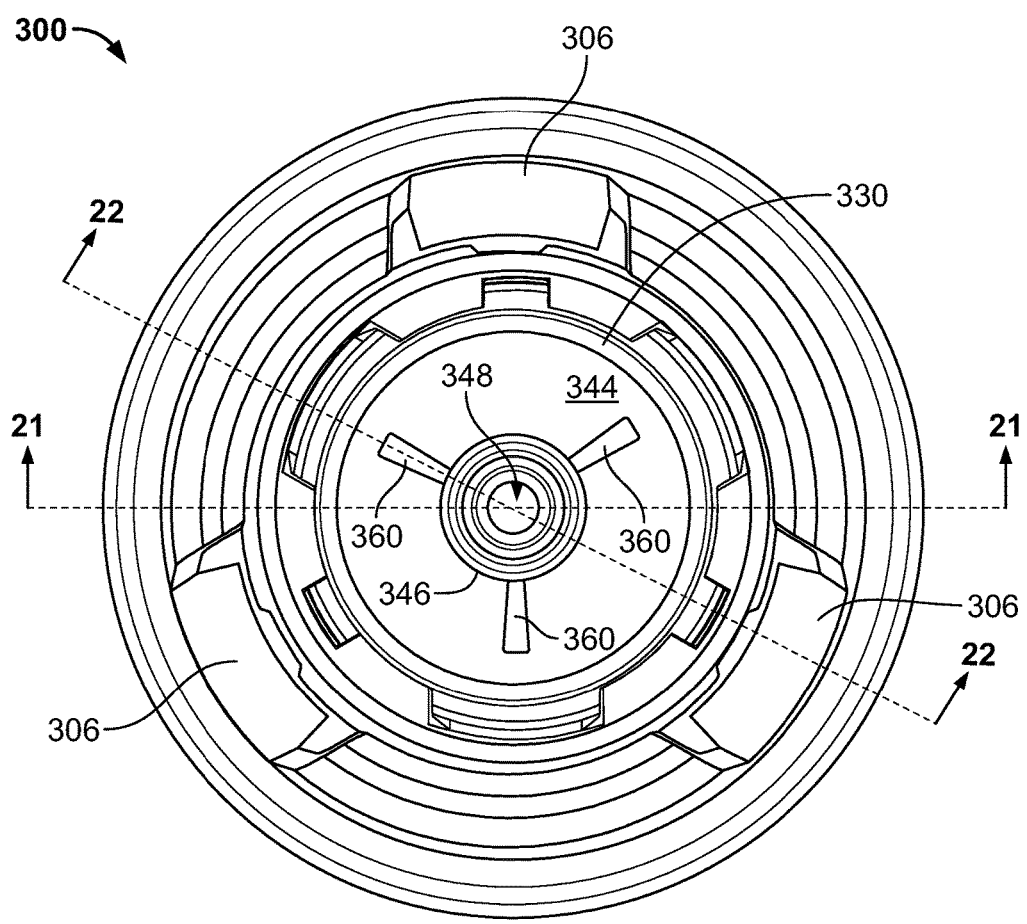
FIG. 19 is a top plan view of the retaining apparatus of FIG. 16.
Figure 20:
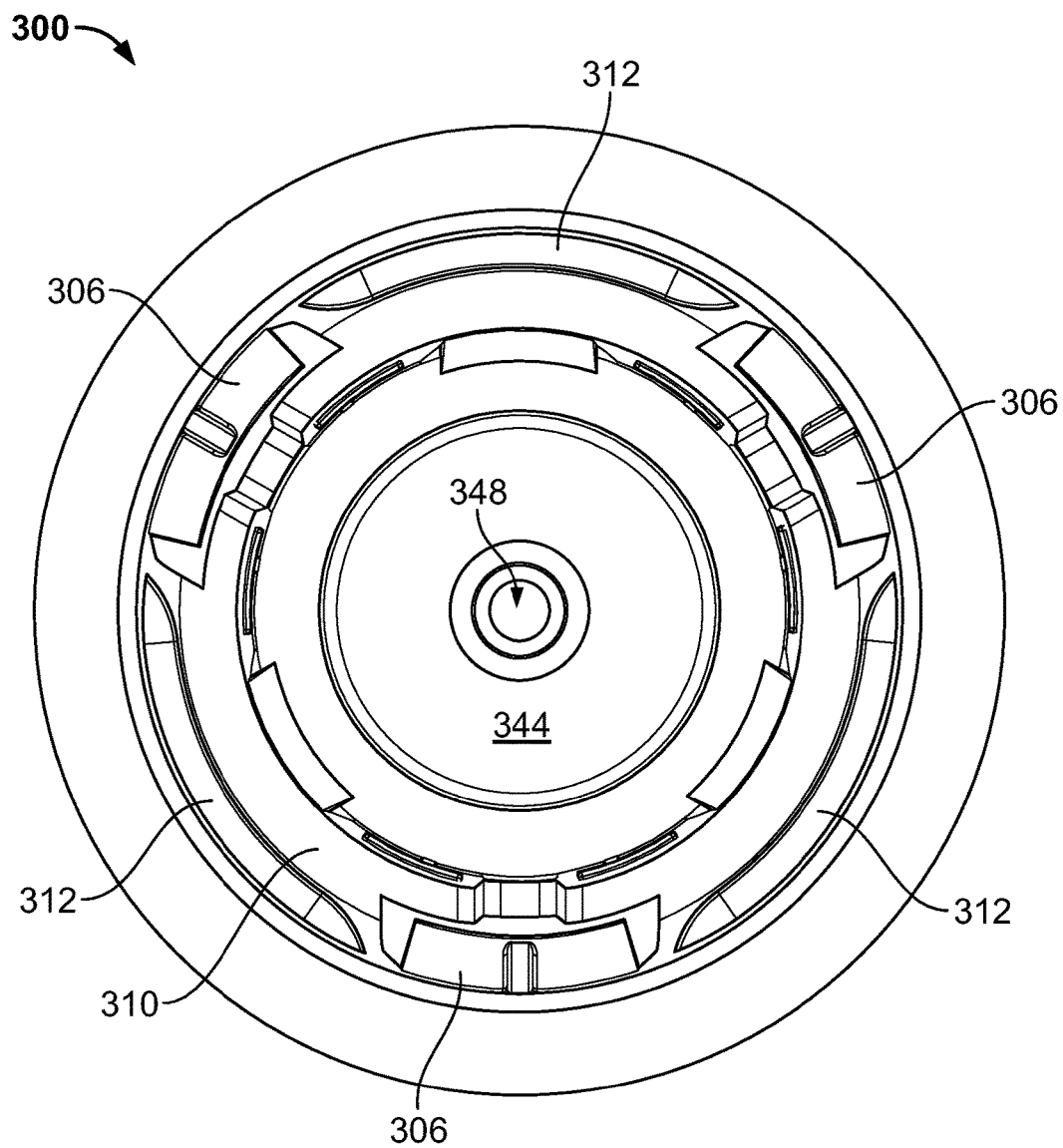
FIG. 20 is a bottom elevational view of the retaining apparatus of FIG. 16.

The bridge section 332 includes a cylindrical side wall 334 and upper retaining lips 336, as seen in FIG. 16. The upper retaining lips 336 and the side wall 334 define an aperture 338 through which the upper portion 330 extends.

Turning again to FIG. 21, the upper portion 330 includes a sidewall 340 having a lower flange 342. The lower flange 342 of the upper sidewall 340 catches the upper retaining lips 336 of the bridge section 332 (see FIG. 21). The upper portion 330 includes a top wall 344. A central tube 346 is disposed on the top wall 344 of the upper portion 330. A dispensing bore 348 is defined by the central tube 346. A lower portion 350 of the dispensing bore 348 is configured to receive the valve stem 112 of the container 100. An upper portion 352 of the dispensing bore 348 is in fluid communication with the valve stem 112 and the central discharge bore 246 of the discharge portion 240 of the top cover 206.

A plurality of upward facing teeth 360 are disposed on the top wall 344 and are coupled to or integrally formed with the central tube 346. In certain embodiments there may only be a single upward facing tooth 360 and the corresponding discharge portion 240 of the base 202 would be configured to receive it.

Figure 23:
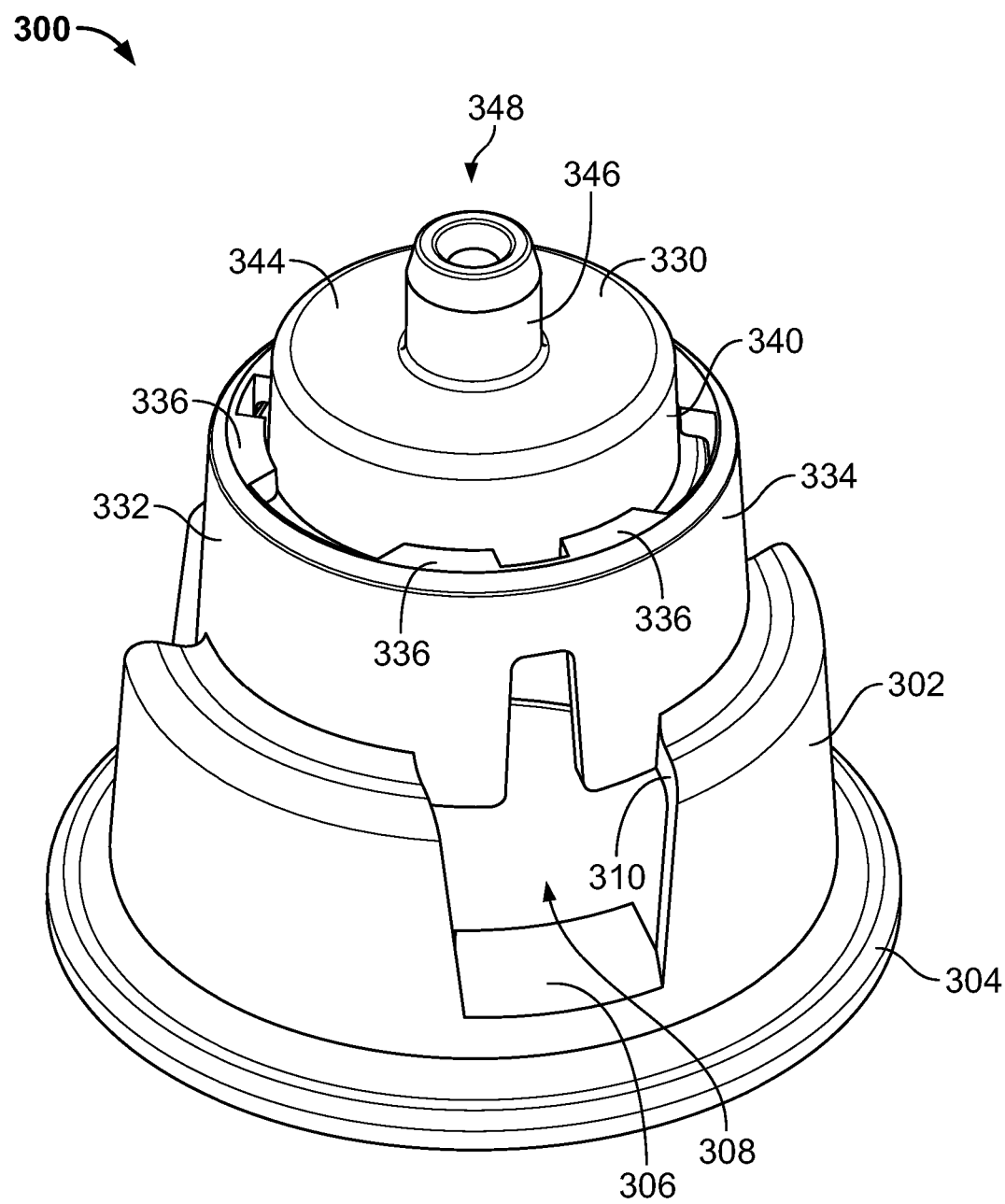
FIG. 23 is an isometric view of another embodiment of a retaining apparatus similar to the embodiment shown in FIG. 16.
Figure 24:
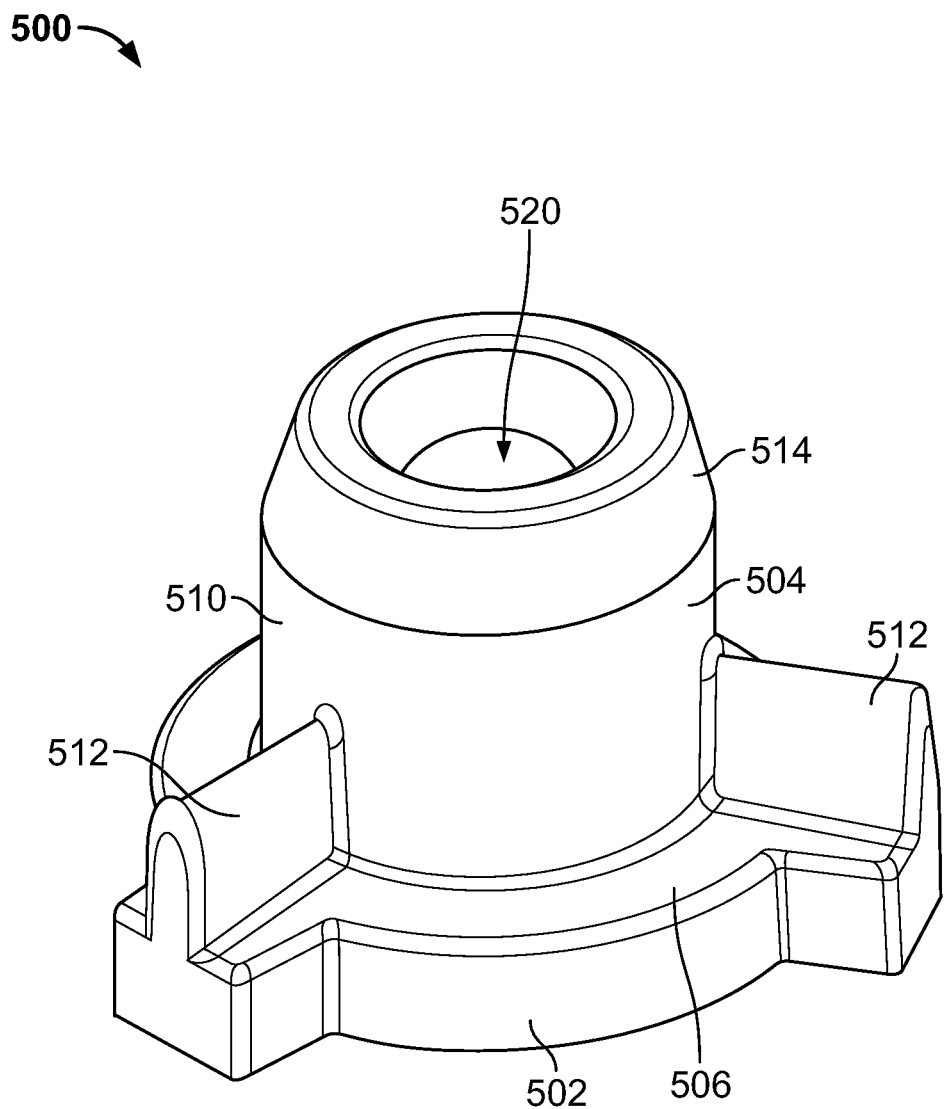
FIG. 24 is an isometric view of yet another embodiment of a retaining apparatus.
Figure 25:
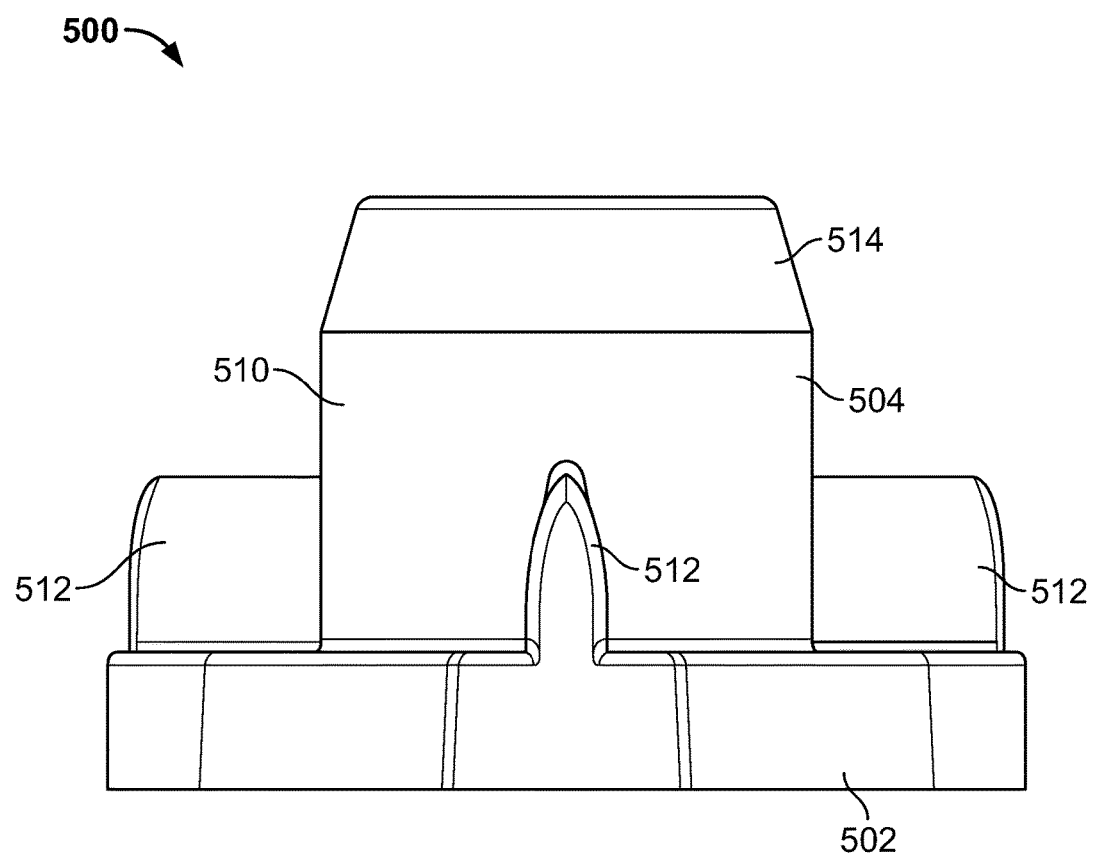
FIG. 25 is a side elevational view of the retaining apparatus of FIG. 24.
Figure 26:
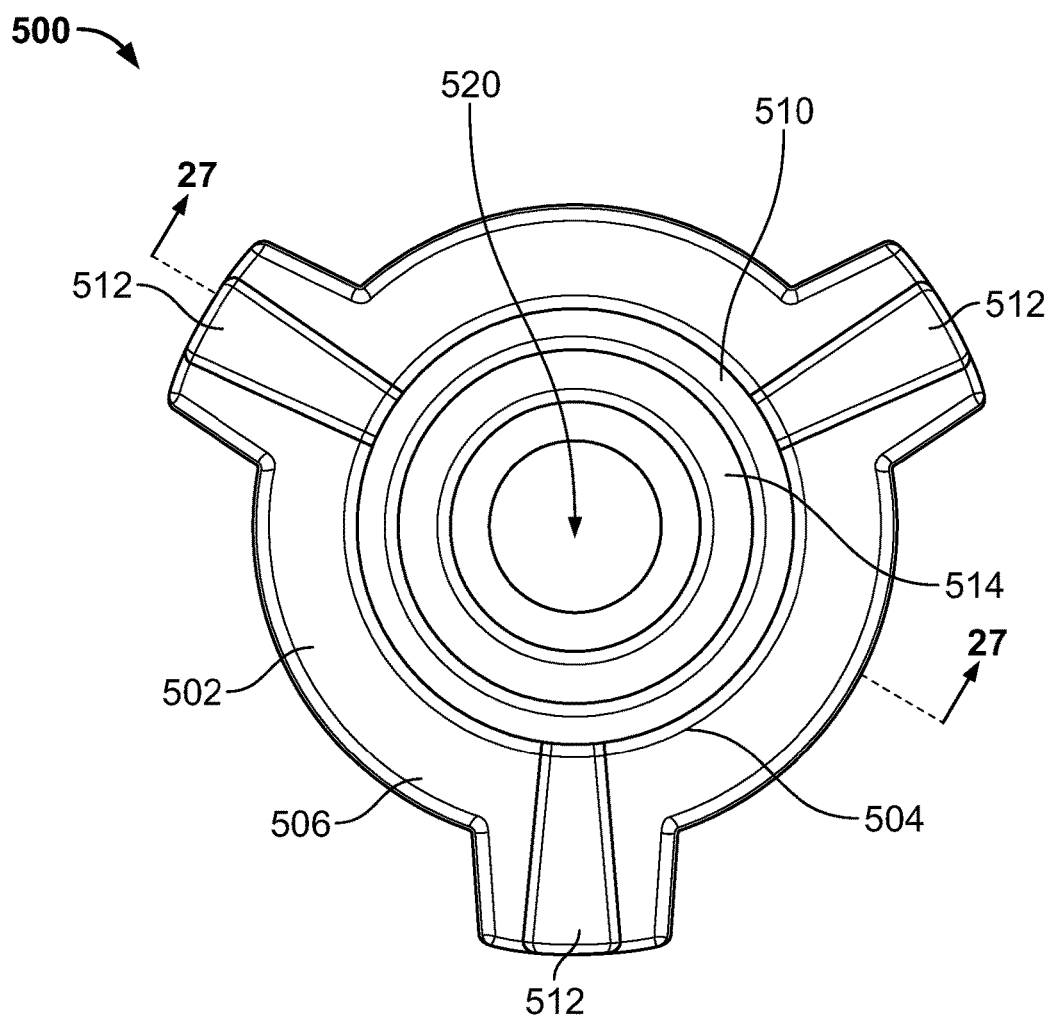
FIG. 26 is a top plan view of the retaining apparatus of FIG. 24.

Another embodiment of the retaining apparatus 300 is depicted in FIG. 23. This embodiment may be substantially the same structurally and operationally as the embodiment depicted in FIGS. 16-22, except that there are no upward facing teeth 360 in FIG. 23.

Regardless of the embodiment, it is contemplated that the actuation of the valve stem 112 of the container 100 is similar to the interaction of the retaining apparatus 216 with the discharge portion 240. Instead of the resilient arms 252 deforming, the upper portion 330 is displaced downward into the bridge portion 332 to allow for actuation of the valve stem 112. It is also contemplated that the retaining apparatus 300 may retain the container 100 in the same configurations as the retaining apparatus 216 within the dispenser 200.

Now turning to FIGS. 24-27, a fourth embodiment of a retaining apparatus 500 is depicted. The retaining apparatus 500 includes a base plate 502. A central tube 504 extends upwards from a top surface 506 of the base plate 502. The central tube 504 defines a dispensing bore 508 having an inside diameter ID (see FIG. 27). An outside diameter OD is defined by an outer surface 510 of the central tube 504 (see FIG. 27). A wall thickness WT is defined as half the difference between the inner diameter ID and the outer diameter OD (see FIG. 27). The retaining apparatus 500 also includes a plurality of upward facing teeth 512 that are coupled to the top surface 506 and the outer surface 510. The central tube may include an upper tapered portion 514. The upper tapered portion 514 serves the same purpose as the angled section 260 of the retaining apparatus 216, which is to form a seal with the angled section 264 of the discharge portion 240 of the dispenser 200.

Figure 27:
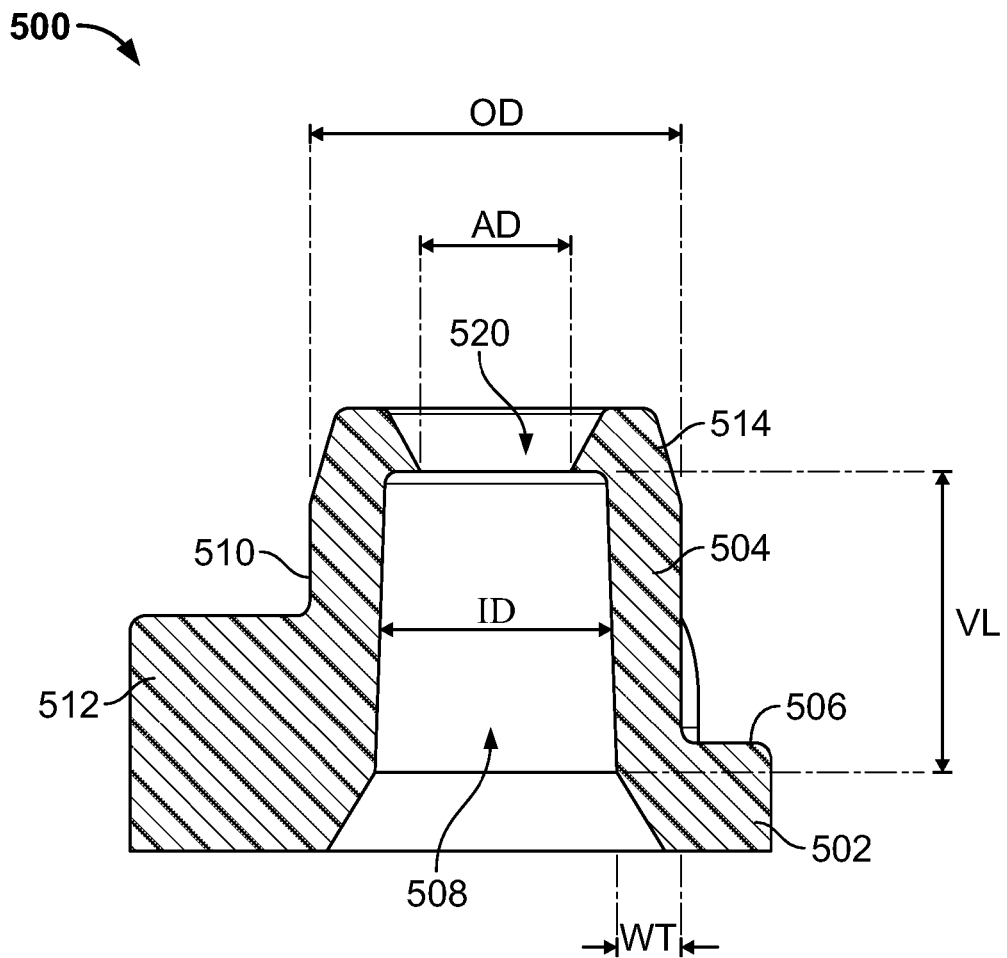
FIG. 27 is a cross-sectional view of the retaining apparatus of FIG. 24 taken along the line 27-27 of FIG. 26.

With reference still to FIG. 27, it is contemplated that the inner diameter ID of the dispensing bore 508 is dimensioned to receive the valve stem 112 of the aerosol container 100. It is also contemplated that by either a friction fit, adhesive, ultra-sonic welding, or any other means know to one having skill in the art, that the inner diameter ID will grip the valve stem in a fashion to support the entire weight of the aerosol container 100 and still maintain a fluid tight seal. Further, the retaining apparatus 500 will form a similar seal and retention relationship between the outer surface 510 of the central tube and the central dispensing bore 246 of the discharge portion 240 of the dispenser 200. It is contemplated that in some embodiments the retaining apparatus 500 may be integrally formed with the valve stem 112.

The inside diameter ID is contemplated to be about 1.4 millimeters (mm). In one embodiment the inside diameter ID is between about 1.1 mm and about 1.7 mm. In a different embodiment the inside diameter ID is between about 0.8 mm and about 2.0 mm. It is also contemplated that the outside diameter OD be about 4.6 mm. In some embodiments the outside diameter OD is between about 4.4 mm and about 4.8 mm. In other embodiments the outside diameter OD is between about 4.2 mm and about 5.0 mm. In one particular embodiment, the inside diameter ID and the outside diameter OD are at least about 0.8 mm and 4.2 mm, respectively. As mentioned above, the wall thickness WT of the central tube 504 is defined as half of the difference between the outside diameter OD and the inside diameter ID. In some embodiments the wall thickness WT is about 1.6 mm. In other embodiments, the wall thickness WT is between about 1.45 mm and about 1.75 mm. In still other embodiments, the wall thickness is at least about 1.45 mm. It is contemplated that the wall thickness WT impacts the ability of the retaining apparatus 500 to survive the insertion process of the valve stem 112 and the insertion of the central tube 504 in the central dispensing bore 246 of the dispenser 200. In fact, insufficient wall thickness WT may result in cracks or failure that prevent the appropriate seals to be formed.

It is also contemplated that the upper tapered portion 514 has a discharge aperture 520 with an aperture diameter AD (see FIG. 27). The aperture diameter AD may be smaller than the inner diameter ID of the dispensing bore 508. However, the discharge aperture 520 allows for the dispensing of fluid that has not fully volatilized or atomized in contrast to many prior art sprayers that include an area of flow restriction provided immediately downstream of the valve stem of an aerosol container to atomize the ejected fluid. The aperture diameter AD is contemplated to be about 0.9 millimeters (mm). In some embodiments the aperture diameter AD is between about 0.8 mm and about 1.0 mm. In other embodiments the aperture diameter AD is between about 0.6 mm and about 1.2 mm. In one particular embodiment the aperture diameter AD is at least about 0.6 mm. It is also contemplated that the aperture diameter AD is related to the exit orifice of the valve stem of the container used in conjunction with the retaining apparatus 500. In fact, it is contemplated that the aperture diameter AD be selected to prevent or substantially prevent the atomization of fluid during dispensing from the valve stem 112 through the discharge aperture 520. Subsequent to the fluids passage though the discharge aperture 520, the fluid may be atomized downstream through other structure. For example, further atomization and/or impartation of certain flow or turbulence characteristics may be imparted to the fluid at the dispensing apertures 208 that are farther downstream from the discharge aperture 520.

Still referring to FIG. 27, the dispensing bore 508 has a vertical length VL of about 1.7 millimeters (mm). In some embodiments the vertical length VL is between about 1.5 mm and about 1.9 mm. In certain embodiments the vertical length VL is between about 1.3 mm and about 2.1 mm. In one particular embodiment, the vertical length VL is at least about 1.3 mm. It is contemplated that the valve stem 112 may be inserted into the dispensing bore 508 about 1.7 mm and, in one embodiment, at least about 1.7 mm. In some embodiments, the valve stem 112 may be inserted into the dispensing bore 508 between about 1.5 mm and about 1.9 mm. In yet other embodiments the valve stem 112 may be inserted into the dispensing bore 508 between about 1.3 mm and about 1.9 mm. In a particular embodiment, the valve stem 112 is inserted into the dispensing bore 508 by at least about 1.3 mm. It is contemplated that in a pre-assembled and pre-actuated state the valve stem 112 will not be fully seated in the dispensing bore 508. The first actuation of the dispenser 200 after purchase or after a new refill is loaded will fully insert the valve stem 112 of the container 100 into the dispensing bore 508. After the first actuation, the friction fit between the valve stem 112 and the dispensing bore 508 will maintain the valve stem 112 fully inserted into the dispensing bore.

Figure 28:
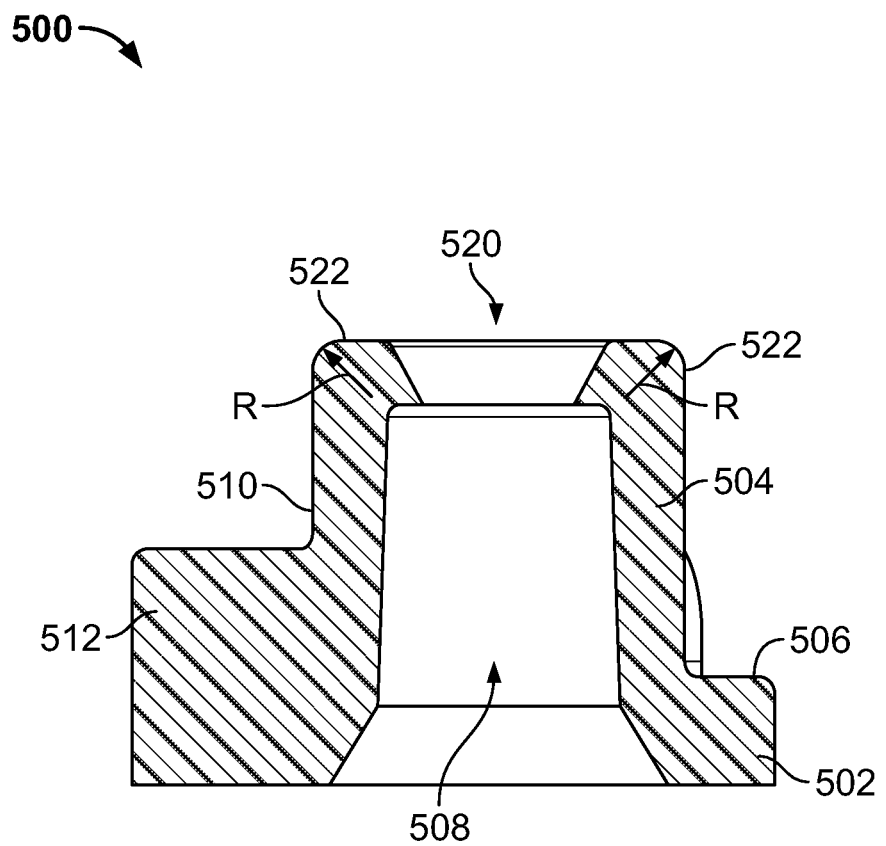
FIG. 28 is a cross-sectional view of another embodiment similar to the one shown in FIG. 27.

Now referring to FIG. 28, another embodiment of the retaining apparatus 500 is depicted. This embodiment may be substantially the same structurally and operationally as the embodiment depicted in FIGS. 24-27, except that the upper tapered portion 514 of the central tube 504 has been replaced with a curved portion 522. The curved portion may have a radius of curvature of about 0.5 mm. In other embodiments the radius of curvature R is between about 0.4 mm and about 1.0 mm. In yet other embodiments the radius of curvature R is between about 0.2 mm and about 1.5 mm. It is contemplated that the curved portion 522 will provide a seal in a similar manner as the upper tapered portion 514 during an actuation step.

It is also anticipated that upon the provision of a container with a retaining apparatus to a consumer, e.g., at a store or through an online purchase, that instructions on how to use the container with retaining apparatus and/or dispenser will be provided. For example, the instructions may indicate that a user is to remove the container with the pre-attached retaining apparatus from a package or to otherwise prepare it for insertion into a dispenser. The instructions may also instruct a user to insert or otherwise place the container and retaining apparatus in functional communication with a dispenser. For example, in connection with the dispenser 200, a user is instructed to: 1) remove the sleeve 204 and top cover 206 from the base plate 210; 2) place the container within the cylindrical wall 212 and rest the flange 220 of the retaining apparatus 216 on an upper end of the wall 212; and 3) place the sleeve 204 and top cover 206 onto the base plate 210. Thereafter, the instructions may inform a user that the device is to be activated to effect a certain outcome within an indoor or outdoor environment. For example, in connection with the dispenser 200, a user may be instructed to press down on the top cover 206 twice to activate the dispenser 200 and cause fluid to be emitted to provide up to eight hours of insect repellency.

Any of the embodiments described herein may be modified to include any of the structures or methodologies disclosed in connection with different embodiments. Further, the present disclosure is not limited to fluid dispensers or fluid dispenser aerosol refill retaining apparatuses of the type specifically shown. Still further, the aerosol refill retaining apparatuses of any of the embodiments disclosed herein may be modified to work with any type of fluid dispenser that utilizes a refill container.

INDUSTRIAL APPLICABILITY

A retaining apparatus is presented that retains an aerosol container for dispensing aerosol material into the surrounding environment from a fluid dispenser. Thus, a user may experience the benefits provided by the material being introduced into the surrounding environment.

Numerous modifications to the present invention will be apparent to those skilled in the art in view of the foregoing description. Accordingly, this description is to be construed as illustrative only and is presented for the purpose of enabling those skilled in the art to make and use the invention and to teach the best mode of carrying out same. The exclusive rights to all modifications which come within the scope of the appended claims are reserved.

We claim:

1. A dispenser, comprising:
    a retaining apparatus including a body portion having an internal bore, the internal bore defining an axial portion having a length in an axial direction and an internal diameter, a tapered surface adjacent the axial portion with a length in the axial direction smaller than the axial portion length, and a wall having a thickness defined between the internal bore and an exterior surface of the body portion, wherein the thickness of the wall is between 1.45 mm and 1.75 mm; and
    an aerosol container having a valve stem, wherein a portion of the valve stem exterior to the aerosol container has a greatest diameter, and wherein the greatest diameter of the valve stem is smaller than the internal diameter of the internal bore,
    wherein a distal end of the portion of the valve stem exterior to the aerosol container is seated within the internal bore.

2. The dispenser of claim 1, wherein the internal diameter is between 1.1 mm and 1.7 mm.

3. The dispenser of claim 1, wherein the body portion further includes an aperture having a diameter between 0.6 mm and 1.2 mm.

4. The dispenser of claim 1, further comprising:
    a collar configured to couple to a sealing cap of the aerosol container,
    wherein the body portion is translatable relative to the collar.

5. The dispenser of claim 4, further comprising:
    a plurality of resilient arms joining the collar to the body portion.

6. A dispenser, comprising:
    a retaining apparatus including a body portion having an internal bore, the internal bore defining an axial portion having a length in an axial direction and an internal diameter, the internal bore further defining a tapered surface adjacent the axial portion with a length in the axial direction smaller than the axial portion length;

an aperture in the body portion having a diameter between 0.6 mm and 1.2 mm; and an aerosol container having a valve stem, wherein a portion of the valve stem exterior to the aerosol container has a greatest diameter, and wherein the greatest diameter of the valve stem is smaller than the internal diameter of the internal bore, wherein a distal end of the portion of the valve stem exterior to the aerosol container is seated within the internal bore.

7. The dispenser of claim 6, wherein the internal diameter is between 1.1 mm and 1.7 mm.

8. The dispenser of claim 6, wherein the body portion includes a wall having a thickness defined between the internal bore and an exterior surface of the body portion.

9. The dispenser of claim 8, wherein the wall thickness is between 1.45 mm and 1.75 mm.

10. The dispenser of claim 6, further comprising:
a collar configured to couple to a sealing cap of the aerosol container,
wherein the body portion is translatable relative to the collar.

11. The dispenser of claim 10, further comprising:
a plurality of resilient arms joining the collar to the body portion.

12. A dispenser, comprising:
a retaining apparatus including a body portion defined between an exterior surface and an internal bore, the internal bore defining an axial portion having a length in an axial direction and an internal diameter and a tapered surface adjacent the axial portion with a length in the axial direction smaller than the axial portion length, the body portion further comprising an upper surface and a frustoconical surface between the upper surface and the exterior surface; and an aerosol container having a valve stem, wherein a portion of the valve stem exterior to the aerosol container has a greatest diameter, and wherein the greatest diameter of the valve stem is smaller than the internal diameter of the internal bore, wherein a distal end of the portion of the valve stem exterior to the aerosol container is seated within the internal bore, and wherein the frustoconical surface is configured to interface with an angled or rounded surface on a dispenser in order to actuate the valve stem.

13. The dispenser of claim 12, wherein the frustoconical surface makes an angle of 15 degrees with respect to a longitudinal axis of the retaining apparatus.

14. The dispenser of claim 12, wherein the internal bore includes an aperture that has a diameter between 0.6 mm and 1.2 mm.

15. The dispenser of claim 12, wherein the body portion has a wall thickness defined between the exterior surface and the interior bore, wherein the wall thickness is between 1.45 mm and 1.75 mm.

16. The dispenser of claim 12, further comprising:
a collar configured to couple to a sealing cap of the aerosol container,
wherein the body portion is translatable relative to the collar.

17. The dispenser of claim 16, further comprising:
a plurality of resilient arms joining the collar to the body portion.

18. The dispenser of claim 1, wherein the internal bore is arranged between the tapered surface and an aperture of the body portion.

19. The dispenser of claim 6, wherein the length of the internal bore is defined between the tapered surface and the aperture.

20. The dispenser of claim 12, wherein the internal bore is arranged between the tapered surface and an aperture of the body portion.

* * * * *